US012778436B2

(12) United States Patent
Hendren et al.

(10) Patent No.: US 12,778,436 B2
(45) Date of Patent: Nov. 3, 2026

(54) IMPLANTABLE CARDIOVASCULAR PRESSURE SENSING SYSTEM AND METHODS OF USE

(71) Applicant: Qura, Inc., Duxbury, MA (US)

(72) Inventors: William G. Hendren, Duxbury, MA (US); Jean-Noel Fehr, Neuchatel (CH); Stefan Bauer, Bern (CH); Douglas P. Adams, Sudbury, MA (US)

(73) Assignee: Qura, Inc., Duxbury, MA (US)

( * ) Notice: Subject to any disclaimer, the term of this patent is extended or adjusted under 35 U.S.C. 154(b) by 0 days.

(21) Appl. No.: 18/695,721

(22) PCT Filed: Aug. 1, 2023

(86) PCT No.: PCT/US2023/071396

§ 371 (c)(1),
(2) Date: Mar. 26, 2024

(87) PCT Pub. No.: WO2024/030883

PCT Pub. Date: Feb. 8, 2024

(65) Prior Publication Data

US 2025/0040816 A1 Feb. 6, 2025

Related U.S. Application Data

(60) Provisional application No. 63/370,053, filed on Aug. 1, 2022.

(51) Int. Cl.

*A61B 5/0215* (2006.01)
*A61B 5/00* (2006.01)

(Continued)

(52) U.S. Cl.

CPC ...... *A61B 5/02152* (2013.01); *A61B 5/02055* (2013.01); *A61B 5/14503* (2013.01);

(Continued)

(58) Field of Classification Search

CPC ............ A61B 5/02152; A61B 5/02055; A61B 5/14503; A61B 5/6852; A61B 5/6869;

(Continued)

(56) References Cited

U.S. PATENT DOCUMENTS 4,127,110 A * 11/1978 Bullara ................ A61B 5/0002 128/903
5,339,818 A * 8/1994 Baker .................... G16H 50/20 600/490

(Continued)

FOREIGN PATENT DOCUMENTS

| | | | |
|---|---|---|---|
| WO | 2010081134 | A1 | 7/2010 |
| WO | 2024030883 | A2 | 2/2024 |
| WO | 2024097185 | A1 | 5/2024 |

OTHER PUBLICATIONS

Hogg et al. "Protective multilayer packaging for long-term implantable medical devices." Surface and Coatings Technology 255 (2014): 124-129.

(Continued)

*Primary Examiner* — Rene T Towa
(74) *Attorney, Agent, or Firm* — Smith Baluch LLP

(57) ABSTRACT

An implantable cardiovascular pressure sensing system can be used to measure blood pressure accurately and safely without any patient intervention. It can include a pressure sensor that makes blood pressure measurements, circuitry for processing and storing the blood pressure measurements, and an antenna for transmitting the processed measurements to an external device (i.e., a device not implanted in the patient). The circuitry can average blood pressure measurements and/or remove artefacts caused by patient motion that is sensed with an accelerometer integrated into implantable cardiovascular pressure sensing system. A multilayer ceramic/polymer coating forms a hermetic seal around the components, preventing leakage or contamination. The (Continued)

implantable cardiovascular pressure sensing system is very versatile: it can be implanted in a blood vessel, next to a blood vessel, in an aneurysm sac, or integrated with another medical implant, such as an Amplatzer septal occluder, and implanted into or next to another vascular structure.

50 Claims, 26 Drawing Sheets

(51) Int. Cl.
*A61B 5/0205* (2006.01)
*A61B 5/145* (2006.01)
*A61B 90/00* (2016.01)
*A61B 5/01* (2006.01)
*A61B 5/11* (2006.01)
*A61B 5/1455* (2006.01)

(52) U.S. Cl.
CPC .......... *A61B 5/6852* (2013.01); *A61B 5/6869* (2013.01); *A61B 5/6876* (2013.01); *A61B 5/721* (2013.01); *A61B 90/06* (2016.02); *A61B 5/01* (2013.01); *A61B 5/11* (2013.01); *A61B 5/14551* (2013.01); *A61B 2560/0219* (2013.01); *A61B 2560/0257* (2013.01); *A61B 2560/045* (2013.01); *A61B 2560/0462* (2013.01); *A61B 2562/0219* (2013.01); *A61B 2562/0247* (2013.01); *A61B 2562/0271* (2013.01); *A61B 2562/168* (2013.01)

(58) Field of Classification Search
CPC ....... A61B 5/6876; A61B 5/721; A61B 90/06; A61B 5/01; A61B 5/11; A61B 5/14551; A61B 2560/0219; A61B 2560/0257; A61B 2560/045; A61B 2560/0462; A61B 2562/0219; A61B 2562/0247; A61B 2562/0271; A61B 2562/168
See application file for complete search history.

(56) References Cited

U.S. PATENT DOCUMENTS

| | | | | |
|---|---|---|---|---|
| 6,024,704 | A * | 2/2000 | Meador | A61B 5/03 128/899 |
| 6,135,966 | A * | 10/2000 | Ko | A61B 5/7267 600/481 |
| 6,159,156 | A * | 12/2000 | Van Bockel | A61B 5/6876 600/481 |
| 6,764,446 | B2 | 7/2004 | Wolinsky et al. | |
| 7,686,762 | B1 | 3/2010 | Najafi et al. | |
| 8,313,819 | B2 | 11/2012 | Hogg et al. | |
| 8,475,374 | B2 | 7/2013 | Irazoqui et al. | |
| 9,078,613 | B2 | 7/2015 | Irazoqui et al. | |
| 9,173,564 | B2 | 11/2015 | Choo et al. | |
| 9,265,428 | B2 | 2/2016 | O'Brien et al. | |
| 9,498,130 | B2 | 11/2016 | Najafi et al. | |
| 9,596,988 | B2 | 3/2017 | Irazoqui et al. | |
| 9,653,926 | B2 | 5/2017 | Park et al. | |
| 9,662,021 | B2 | 5/2017 | Chow et al. | |
| 10,022,054 | B2 | 7/2018 | Najafi et al. | |
| 10,044,227 | B2 | 8/2018 | Chappell et al. | |
| 10,426,341 | B2 | 10/2019 | Choo et al. | |
| 10,478,067 | B2 | 11/2019 | Najafi | |
| 10,687,709 | B2 | 6/2020 | Najafi | |
| 10,797,522 | B2 | 10/2020 | Chappell et al. | |
| 10,973,425 | B2 | 4/2021 | Cao | |
| 11,497,399 | B2 | 11/2022 | Adams et al. | |
| 11,517,269 | B2 | 12/2022 | Adams et al. | |
| 11,554,009 | B2 | 1/2023 | Harant et al. | |
| 11,602,427 | B2 | 3/2023 | Adams et al. | |
| 11,684,703 | B2 | 6/2023 | Adams et al. | |
| 11,806,278 | B2 | 11/2023 | Adams et al. | |
| 2004/0133092 | A1* | 7/2004 | Kain | H01F 17/0006 600/377 |
| 2005/0159789 | A1 | 7/2005 | Brockway et al. | |
| 2009/0177225 | A1* | 7/2009 | Nunez | A61B 5/6862 606/213 |
| 2010/0137694 | A1 | 6/2010 | Irazoqui et al. | |
| 2011/0105927 | A1* | 5/2011 | Greenhut | A61N 1/3702 600/513 |
| 2011/0313322 | A1* | 12/2011 | Fossan | G09B 23/288 600/587 |
| 2015/0289772 | A1* | 10/2015 | Huang | A61B 5/6884 600/478 |
| 2015/0351645 | A1* | 12/2015 | Hiltner | A61M 25/09 600/486 |
| 2016/0000344 | A1* | 1/2016 | Cao | A61B 3/16 600/587 |
| 2017/0164831 | A1 | 6/2017 | Choo et al. | |
| 2017/0209045 | A1 | 7/2017 | Choo et al. | |
| 2018/0035888 | A1 | 2/2018 | Irazoqui et al. | |
| 2018/0117341 | A1* | 5/2018 | Kane | A61B 7/00 |
| 2018/0168463 | A1 | 6/2018 | Morris et al. | |
| 2019/0247664 | A1 | 8/2019 | Irazoqui et al. | |
| 2020/0237218 | A1 | 7/2020 | Irazoqui et al. | |
| 2021/0137379 | A1 | 5/2021 | Fehr et al. | |
| 2021/0307609 | A1 | 10/2021 | Adams et al. | |
| 2022/0054007 | A1* | 2/2022 | Adams | A61B 5/721 |
| 2022/0176088 | A1 | 6/2022 | Salahieh et al. | |
| 2023/0024683 | A1 | 1/2023 | Adams et al. | |
| 2023/0309827 | A1 | 10/2023 | Irazoqui et al. | |

OTHER PUBLICATIONS

International Search Report and Written Opinion in International App. No. PCT/US2023/071396 mailed Jan. 19, 2024, 22 pages.
Beier et al. "Preliminary characterization of a glucose-sensitive hydrogel." 2010 Annual International Conference of the IEEE Engineering in Medicine and Biology. IEEE, 2010, 4 pages.
Chow et al "High data-rate 6.7 GHz wireless ASIC transmitter for neural prostheses." 2007 29th Annual International Conference of the IEEE Engineering in Medicine and Biology Society. IEEE, 2007, 4 pages.
Chow et al. "A miniature-implantable RF-wireless active glaucoma intraocular pressure monitor." IEEE Transactions on Biomedical Circuits and Systems 4.6 (2010): 340-349.
Chow et al. "Commercial development of RF medical implantable devices." 2013 IEEE MTT-S International Microwave Workshop Series on RF and Wireless Technologies for Biomedical and Healthcare Applications (IMWS-BIO). IEEE, 2013, 3 pages.
Chow et al. "Evaluation of cardiovascular stents as antennas for implantable wireless applications." IEEE Transactions on Microwave Theory and Techniques 57.10 (2009): 2523-2532.
Chow et al. "Fully wireless implantable cardiovascular pressure monitor integrated with a medical stent." IEEE Transactions on Biomedical Engineering 57.6 (2010): 1487-1496.
Chow et al. "High frequency transcutaneous transmission using stents configured as a dipole radiator for cardiovascular implantable devices." 2009 IEEE MTT-S International Microwave Symposium Digest. IEEE, 2009, 4 pages.
Chow et al. "Miniature antenna for RF telemetry through ocular tissue." 2008 IEEE MTT-S International Microwave Symposium Digest. IEEE, 2008, 4 pages.
Chow et al. "Mixed-signal integrated circuits for self-contained sub-cubic millimeter biomedical implants." 2010 IEEE International Solid-State Circuits Conference—(ISSCC). IEEE, 2010, 3 pages.
Chow et al. "Toward an implantable wireless cardiac monitoring platform integrated with an FDA-approved cardiovascular stent." Journal of interventional cardiology 22.5 (2009): 479-487.
Chow, Eric Y., et al. "Wireless powering and the study of RF propagation through ocular tissue for development of implantable sensors." IEEE Transactions on Antennas and Propagation 59.6 (2011): 2379-2387.
Chow, et al. "Implantable wireless telemetry boards for in vivo transocular transmission." IEEE Transactions on Microwave Theory and Techniques 56.12 (2008): 3200-3208.

(56) References Cited

OTHER PUBLICATIONS

Conovaloff et al. "Effects of a synthetic bioactive peptide on neurite growth and nerve growth factor release in chondroitin sulfate hydrogels." Biomatter 1.2 (2011): 165-173.
Decarlo et al. "Development of a Microfluidic Ion Sensor Array (MISA) to Monitor Gravity-Dependent Calcium Fluxes in Ceratopteris Spores." Gravitational and Space Biology 1089 (2006): 2 pages.
Dresher et al. "A compact nanopower low output impedance CMOS operational amplifier for wireless intraocular pressure recordings." 2007 29th Annual International Conference of the IEEE Engineering in Medicine and Biology Society. IEEE, 2007, 4 pages.
Gafton et al. "Portable microfluidic cytometer for whole blood cell analysis." Microfluidics, BioMEMS, and Medical Microsystems VIII. vol. 7593. SPIE, 2010., 8 pages.
Graves et al. "Electrically mediated neuronal guidance with applied alternating current electric fields." Annals of Biomedical Engineering 39.6 (2011): 1759-1767.
Ha et al. "3D packaging technique on liquid crystal polymer (LCP) for miniature wireless biomedical sensor." 2010 IEEE MTT-S International Microwave Symposium. IEEE, 2010, 4 pages.
Ha et al. "Polymer-based miniature flexible capacitive pressure sensor for intraocular pressure (IOP) monitoring inside a mouse eye." Biomedical microdevices 14.1 (2012): 207-215.
Ha et al. "Power distribution to multiple implanted sensor devices using a multiport bandpass filter (BPF) approach." 2014 IEEE MTT-S International Microwave Symposium (IMS2014). IEEE, 2014, 5 pages.
Hassell et al. et al. "Constant-current adjustable-waveform microstimulator for an implantable hybrid neural prosthesis." 2007 29th Annual International Conference of the IEEE Engineering in Medicine and Biology Society. IEEE, 2007, 4 pages.
Hirayama et al, "Permeation properties to CO2 and N2 of polyethylene oxide containing and cross-linked polymer films", in Journal of Membrane Science, 1999; 160, pp. 87-99.
Irazoqui et al. "In-vivo EEG recording using a wireless implantable neural transceiver." First International IEEE EMBS Conference on Neural Engineering, 2003. Conference Proceedings . . . IEEE, 2003, 4 pages.
Irazoqui et al. "Recording brain activity wirelessly." IEEE Engineering in Medicine and Biology Magazine 24.6 (2005): 48-54.
Irazoqui et al. "Transcutaneous RF-powered neural recording device." Proceedings of the Second Joint 24th Annual Conference and the Annual Fall Meeting of the Biomedical Engineering Society][Engineering in Medicine and Biology. vol. 3. IEEE, 2002. 3 pages.
Jaroch et al. "Magnetic insertion system for flexible electrode implantation." Journal of neuroscience methods 183.2 (2009): 213-222.
Jedlicka et al. "Calibration of neurotransmitter release from neural cells for therapeutic implants." International journal of neural systems 19.03 (2009): 197-212.
Judy et al. "Ferromagnetic micromechanical magnetometers." Solid-State Sensor and Actuator Workshop (Hilton Head Island, SC, USA). 2000, 2 pages.
Kahn et al. "Low-power, high data rate transceiver system for implantable prostheses." International journal of telemedicine and applications 2010, 9 pages.
Markandeya, Himanshu, et al. "Low-power DWT-based quasi-averaging algorithm and architecture for epileptic seizure detection." Proceedings of the 16th ACM/IEEE international symposium on Low power electronics and design. 2010, 6 pages.
Mei et al. "Miniaturizing wireless implants." Nature biotechnology 32.10 (2014): 1008-1010.
Musick et al. "Sensor to detect endothelialization on an active coronary stent." BioMedical Engineering OnLine 9.1 (2010): 1-7.
Raghunathan et al. "The design and hardware implementation of a low-power real-time seizure detection algorithm." Journal of neural engineering 6.5 (2009): 056005, 13 pages.
Raghunathan et al. "Ultra low-power algorithm design for implantable devices: Application to epilepsy prostheses." Journal of Low Power Electronics and Applications 1.1 (2011): 175-203.
Rajdev et al. "Effect of stimulus parameters in the treatment of seizures by electrical stimulation in the kainate animal model." International journal of neural systems 21.02 (2011): 151-162.
Rokkam et al. "High-density data acquisition system and signal preprocessor for interfacing with microelectromechanical system-based biosensor arrays." Review of scientific instruments 78.4 (2007): 044303, 9 pages.
Ul Haque et al. "A MEMS fabricated cell electrophysiology biochip for in silico calcium measurements." Sensors and Actuators B: Chemical 123.1 (2007): 391-399.
Ul Haque et al. "Design, fabrication and characterization of an in silico cell physiology lab for bio sensing applications." Journal of Physics: Conference Series. vol. 34. No. 1. IOP Publishing, 2006, 7 pages.
Ward et al. "Evolving refractory major depressive disorder diagnostic and treatment paradigms: toward closed-loop therapeutics." Frontiers in neuroengineering (2010): 15 pages.
Ward et al. "Toward a comparison of microelectrodes for acute and chronic recordings." Brain research 1282 (2009): 183-200.
Yang et al. "RF powering for embedded glaucoma sensors in miniature packages." Proc. Union Radio Scientifique Internationale General Assembly (2008), 4 pages.
Extended European Search Report in European App. No. 23850890.7 dated Mar. 6, 2026, 10 pages.

* cited by examiner

IMPLANTABLE CARDIOVASCULAR PRESSURE SENSING SYSTEM AND METHODS OF USE

CROSS-REFERENCE TO RELATED PATENT APPLICATION(S)

This patent application is a U.S. national stage filing under 35 U.S.C. 371 of PCT/US2023/071396, filed Aug. 1, 2023, and entitled "IMPLANTABLE CARDIOVASCULAR PRESSURE SENSING SYSTEM AND METHODS OF USE," which claims the priority benefit, under 35 U.S.C. 119 (e), of U.S. Application No. 63/370,053, filed Aug. 1, 2022, which is incorporated herein by reference in its entirety for all purposes.

BACKGROUND

Cardiovascular diseases (CVDs) are the leading cause of mortality, representing 32% of deaths globally. CVDs are a group of disorders of the heart and blood vessels and include hypertension, congestive heart failure, stroke, diseases of the arteries, and others. A common element to many of these diseases is the occurrence of abnormal pressures in cardiovascular structures, either as a cause of or as secondary to the underlying disease. Measurement of these pressures is a cornerstone of treatment regimens.

Blood pressure (BP), for example, is among the most important physiologic parameters in the living body. Hypertension (HTN) or high blood pressure is the leading cause of mortality and morbidity in the world today. Treatment of HTN depends on the accurate and reliable measurement of BP in a simple and reproducible manner and is the cornerstone to reducing the cardiovascular complications of patients with this condition.

Similarly, congestive heart failure (CHF) is a complex clinical syndrome in which the heart cannot pump enough blood to meet the body's requirements. A key hallmark of CHF is that the pressures in affected cardiac chambers are elevated reflecting the heart muscle's inability to pump properly. Measurement of the pressures in the heart chambers indirectly or directly is not only diagnostic of the condition, but also can serve as a guide to effective treatment for the condition.

Measurement of cardiovascular pressures is useful for the diagnosis and subsequent treatment of a large range of cardiovascular diseases. The methodologies range from simple cuff measurement of BP with a sphygmomanometer to implantable pressure sensors placed invasively. Established invasive methodologies include placement of highly sensitive implants in the heart or lungs to measure right ventricular pressure (RVP), left atrial pressure (LAP), pulmonary artery pressure (PAP), pulmonary capillary wedge pressure (PCWP), and central venous pressure (CVP). Additionally, implantable pressure sensors have been used to monitor pressure in aneurysms post-endovascular repair.

The vast majority of these invasive methodologies are designed and used for acute or short-term measurement and use cases. For example, it is the standard of care for patients undergoing open heart surgery to have temporary catheters, such as Swan-Ganz catheters, or inter-arterial lines placed for intra and peri-operative monitoring of specific cardiovascular pressures. However, fully implanted sensors and systems for measurement of pressures long-term in patients with chronic cardiovascular diseases, such as hypertension or congestive heart failure, are less developed and in clinical use because of a number of different challenges in the design and engineering of such systems.

As an example, the CardioMEMS HF system measures PAP for the management of CHF. The CardioMEMS HF system is composed of flexible plates bearing inductor windings within a hermetically sealed cavity. They are fused in a silica matrix while a nitinol basket encompasses the system's electronic components. Pressure-dependent changes in resonant frequencies are directionally proportional to pressure changes within the pulmonary artery and are detected using an external antenna activated by the sensor over a radio-frequency impulse. The CardioMEMS HF system does not have any batteries or leads. It is powered by radio-frequency signals from an external antenna. While pioneering in concept when first introduced to the market, the CardioMEMS HF system cannot make continuous measurements or measurements over time. The CardioMEMS HF system also requires significant patient engagement to generate and report data. In addition, the CardioMEMS HF system is very expensive and has been associated with post-implant adverse events.

SUMMARY

Unlike other sensors, the implantable cardiovascular pressure sensing systems disclosed here can measure real-time patient pressure data continuously. Inventive implantable cardiovascular pressure sensing systems can generate a far higher quality assessment of patient disease state and treatment efficacy. Each inventive implantable cardiovascular pressure sensing system incorporates a pressure sensor that is sensitive and accurate over a desired range of pressure readings and electronic components that are hermetically sealed, including a rechargeable power supply and a processor for reading the targeted pressure measurements. The processor can be paired with innovations in wireless technologies, current mobile technologies, and data management, including the use of artificial intelligence to analyze data.

An inventive implantable cardiovascular pressure sensing system offers ease of use, high data quality and utilization, and little to no need for patient engagement or interaction. Reducing or eliminating patient engagement or interaction reduces cost and reduces or eliminates the problem of patient non-compliance. Inventive systems are biocompatible and can be implanted easily, improving patient comfort.

Embodiments of the inventive technology include a system with a pressure sensor, circuitry, hermetic sealing and coating, rechargeable battery, gel and/or liquid, and antenna. This system is designed for frequent, automatically generated, high-quality pressure data measurement that is wirelessly transmitted externally to the cloud and output devices in a way that makes the data is highly actionable remotely and in real-time. The system is designed to maximize ease of use and comfort for both patients and physicians to positively impact the management of patients with a range of cardiovascular diseases.

The present technology includes an implantable cardiovascular pressure sensing system ("sensing system") that is configured to be implanted into a patient to measure a specified cardiovascular pressure continually and autonomously over a long period. The sensing system may be implanted against the outer wall of a blood vessel, inside of a blood vessel (e.g., inside of an artery or vein), or inside of the heart. As an example, the sensing system that resides on against the outer wall of a blood vessel or inside of a blood vessel may be used to monitor BP in the care of patients with HTN. As another example, a sensing system that resides in the heart or one of the great vessels of the heart may be used to monitor heart failure or primary pulmonary artery hypertension. The sensing system may collect pressure measurements, store those measurements locally, and transmit those measurements wirelessly to an external device where they can be viewed by the patient or a healthcare provider. The measurement data may be analyzed to determine current disease states and/or guide for optimal patient therapies. In this way, patient therapies can be highly personalized with the goal of improving clinical outcomes, reducing costs, increasing patient quality of life, and simplifying the physicians care of these patients with these challenging diseases.

An inventive device may include a pressure sensor, circuitry, rechargeable battery, gel (e.g., silicone gel) and/or liquid, antenna, and coating. The pressure sensor has at least one sensing surface and is configured to measure a range of desired pressures (e.g., for BP measurement, a range of pressure of about 40 mm Hg to about 250 mm Hg; for LA or PAP a range of 0 mm Hg to 40 or 50 mm Hg). The circuitry is in electrical communication with the pressure sensor. The rechargeable battery is configured to provide power to the pressure sensor and the circuitry. The gel and/or liquid is disposed on the sensing surface comprises water in a weight percent of about 0.001% by weight to about 5% by weight. The antenna is in electrical communication with the rechargeable battery and the circuitry. And a biocompatible, multilayer coating, which comprises parylene and $SiO_x$, is disposed on at least the gel and/or liquid and forms an outer layer of the device and hermetically seals the device.

An inventive method of measuring cardiovascular pressure may include collecting cardiovascular pressure measurements inside of a subject's cardiovascular system with a device for sensing cardiovascular pressure; averaging cardiovascular pressure measurements with the device; wirelessly transferring averaged cardiovascular pressure measurements from the device to an external device; and wirelessly recharging a power source in the device.

An implantable cardiovascular pressure sensing system can be implanted using a variety of approaches. For instance, an inventive sensing system can be inserted into a human per percutaneous insertion or open approaches; placed in contact with or close vicinity to a blood vessel (e.g., any artery or vein in the body, including a natural or synthetic blood vessel); and fixed in place with a direct suture technique or bio-adhesive. The sensing system can also be incorporated in a device, such as a stent or Amplatz device, that is implanted using known techniques.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

DETAILED DESCRIPTION

Figure 1A:
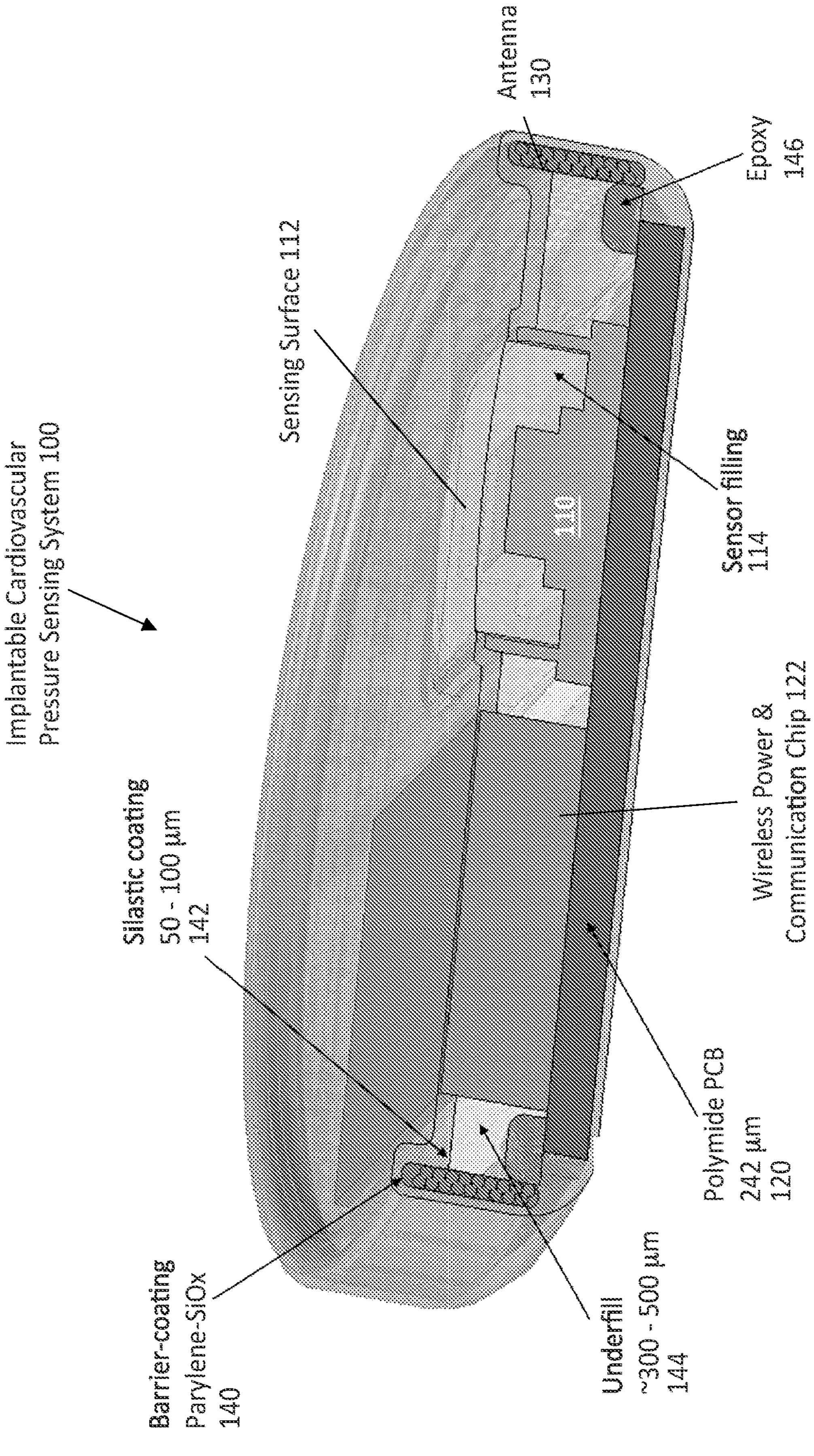
FIG. 1A illustrates an inventive implantable cardiovascular pressure sensing system.
Figure 1B:
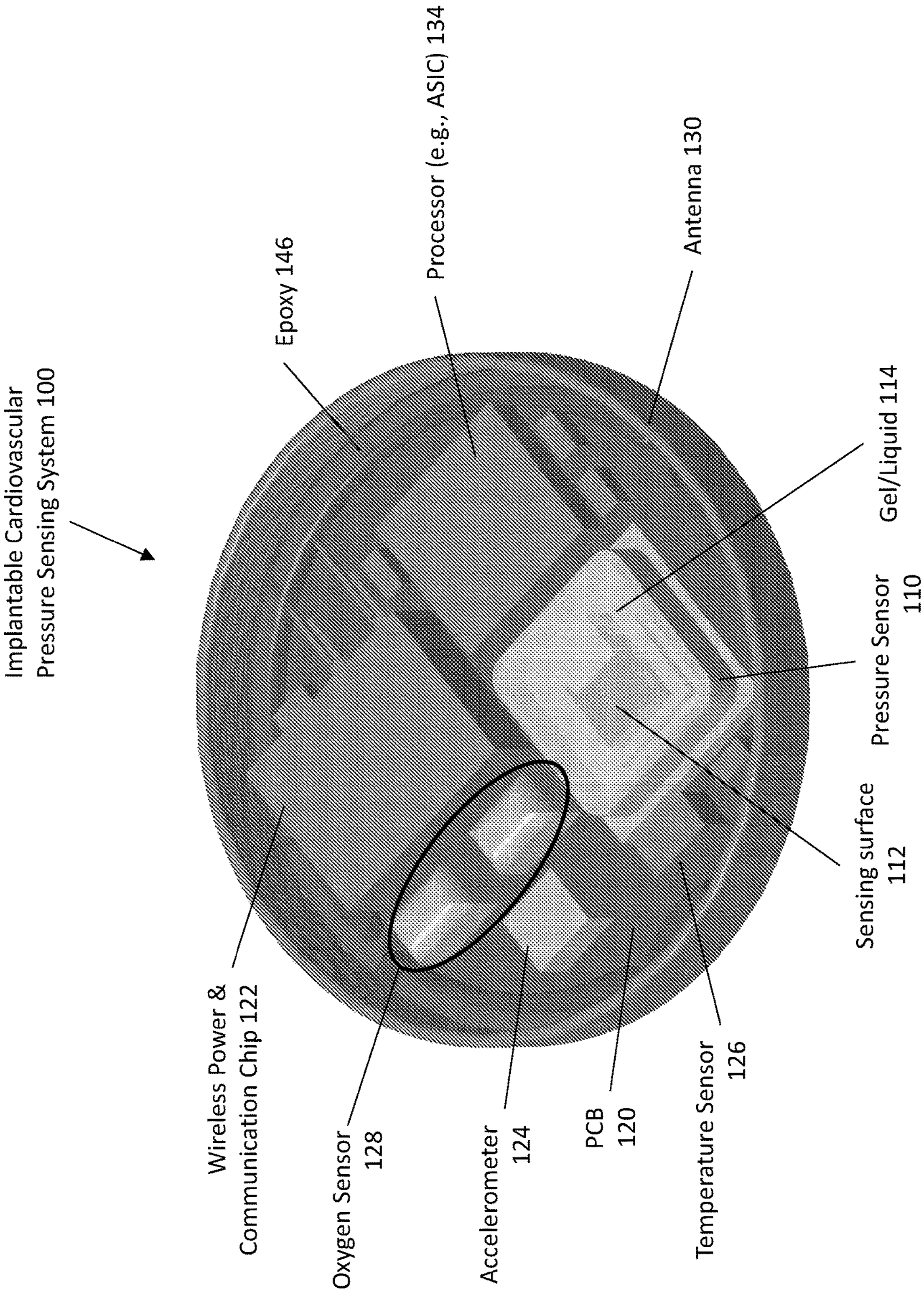
FIG. 1B illustrates the electronic components and substrate of the implantable cardiovascular pressure sensing system in FIG. 1A.

FIGS. 1A and 1B illustrates a first inventive cardiovascular pressure sensing system 100, or simply sensing system 100. The sensing system 100 includes a polyimide printed circuit board (PCB) 120 having a thickness of about 242 μm with several electronic components disposed on and secured to the PCB 120 with solder. The electronic components on the PCB 120 may be electrically connected to each other via conductive traces on the PCB 120. The sensing system 100 may also include other electronic components that are electrically connected to the PCB 120 and/or to electronic components on the PCB 120 but are not on the PCB 120 themselves. The electronic components both on and off the PCB 120 may include, for example, a pressure sensor 110, a rechargeable battery or other power supply, a processor 134, a wireless power and communication chip or transceiver 122, an accelerometer 124, a temperature sensor 126, and an oxygen sensor 128. In this example, the oxygen sensor 128 is an optical oxygen sensor with a light source (e.g., a light-emitting diode) for illuminating the blood vessel and a photodetector for detecting light scattered and/or reflected by the blood vessel.

The sensing system 100 may include an antenna 130, which can be implemented as a circular coil of conductive metal (e.g., gold or copper) that approximately traces the edges of the PCB 120 and is held in place with epoxy 146. In this way, the coiled antenna 130 forms a wall that defines a perimeter of the sensing system 100. An underfill 144 is disposed on at least part of a surface of the PCB 120 and at least some of the electronic components. The underfill 144 may be contained within the perimeter formed by the coiled antenna. A separate sensor filling material 114 is disposed on the pressure sensor's sensing surface 112.

Unlike other implantable devices, the sensing system 100 may not have a rigid housing or casing. Instead of a rigid housing or casing, the sensor system 100 has a multilayer coating 140 disposed on the filling material 144 and exposed surfaces of the antenna 130, PCB 120, and/or electronic components on the PCB 120. This multilayer coating 140 is formed of alternating layers of ceramic (e.g., silicon dioxide) and polymer (e.g., Parylene-C, which is a chlorinated poly (para-xylylene) polymer) and forms the outer surface of the sensing system 100. As explained in greater detail below, the multilayer coating 140 is flexible and hermetically seals the sensing system 100, preventing the sensing system's contents (e.g., the filling material) from leaking out and water from diffusing in. The multilayer coating 140 gives the sensing system 100 several advantages over other implantable sensing systems, including (1) improved sensor sensitivity; (2) improved wireless transmission of power and data; (3) extreme miniaturization (smaller volume); and (4) lower production costs.

Optionally, a silastic coating 142 may be disposed on the sensing system 100 on an inner or outer surface of the multilayer coating 140. In FIG. 1A, for example, the silastic coating 142 has a thickness of about 50-100 μm and is between the underfill 144 and the multilayer coating 140, but not necessarily between the multilayer coating 140 and the sensor filling material 114. In this position, the silastic coating 142 acts as an adhesion layer that helps the multilayer coating 140 to stick fast to the filling material 144.

The filling material 114 and multilayer coating 140 are deformable materials that allow pressure to be communicated from the environment outside of the sensing system 100 to the pressure sensor 110 in the sensing system 100. The multilayer coating 140 is thin and flexible enough that it transmits pressure P exerted by in environment outside of the sensing system 100 to the sensor filling material 114, which transmits the pressure to the pressure sensor's sensing surface 112.

Figure 2A:
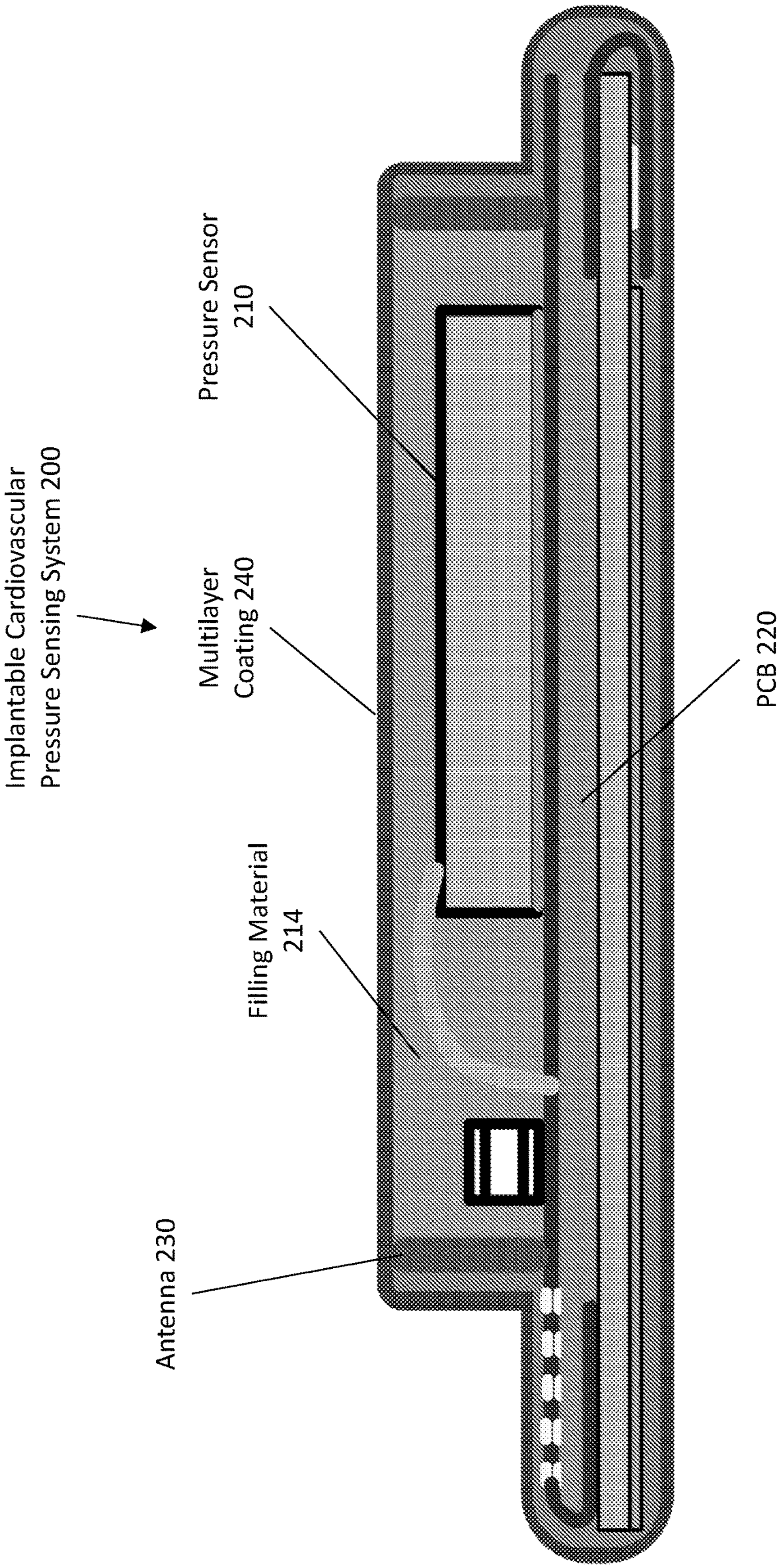
FIG. 2A illustrates a second version of implantable cardiovascular pressure sensing system.
Figure 2B:
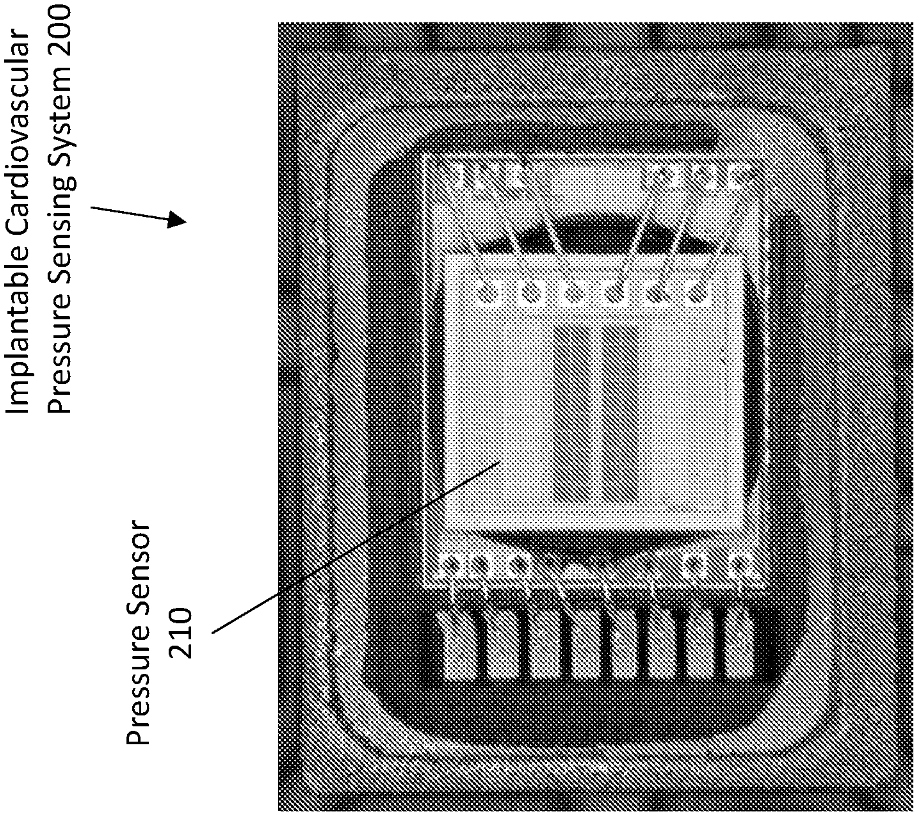
FIG. 2B is a photograph of an example of the pressure sensing membrane of the implantable cardiovascular pressure sensing systems of FIG. 2A.
Figure 2C:
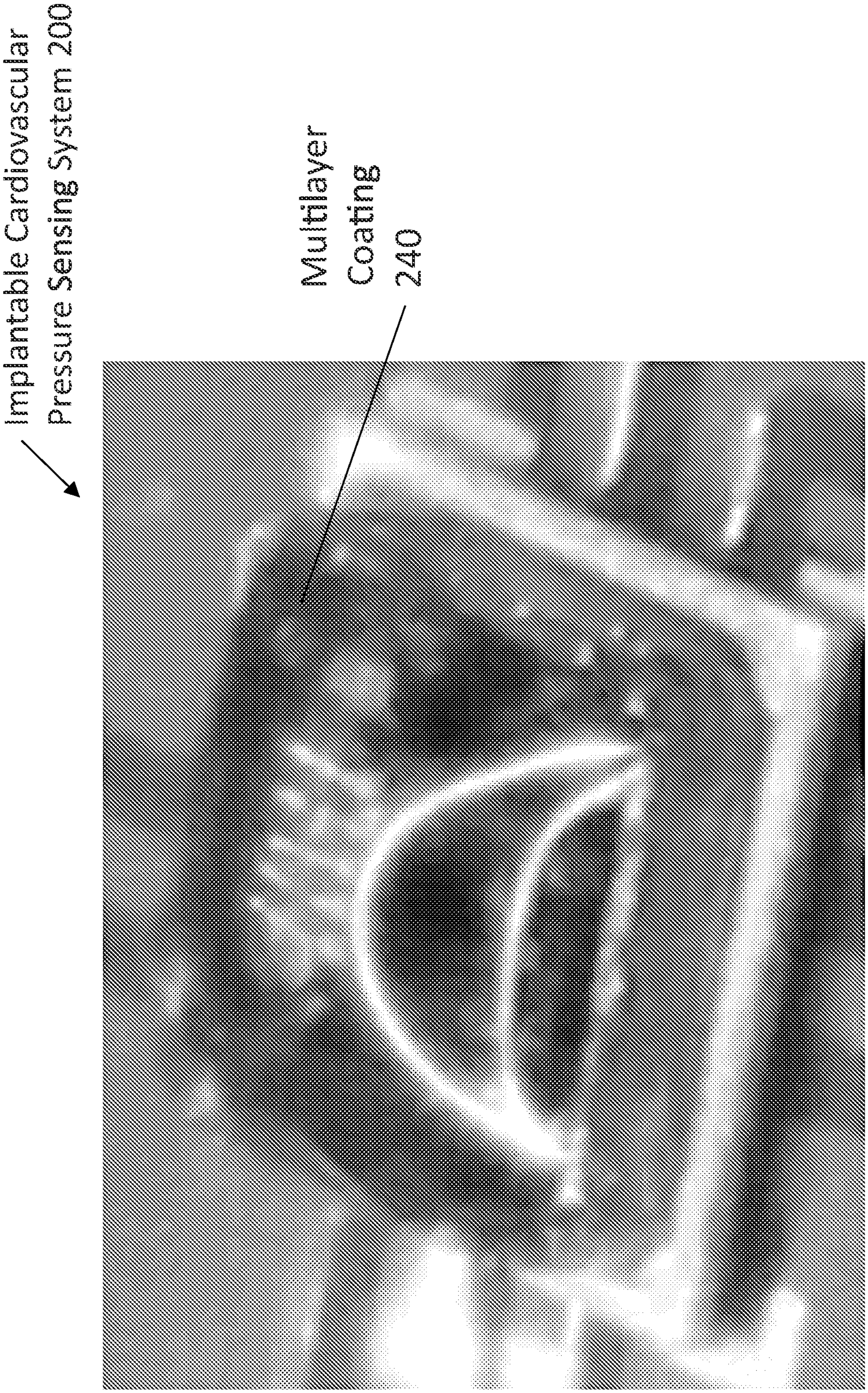
FIG. 2C is another photograph of an example of the pressure-sensing membrane of the implantable cardiovascular pressure sensing system of FIG. 2A, where the pressure-sensing membrane is covered with a silicone gel.

FIGS. 2A-2C illustrate another inventive cardiovascular pressure sensing system 200. Like the sensing system 100 in FIGS. 1A and 1B, the sensing system 200 in FIGS. 2A-2C can include electronic components, such as a pressure sensor 210 and a transceiver, and an antenna 230 disposed on a PCB 220. The pressure sensor 210 can be implemented as a microelectromechanical system (MEMS) capacitive pressure sensor with dimensions on the microscale. The sensing system 200 may also include a processor or microcontroller, an accelerometer, an oxygen sensor, a temperature sensor, and/or other circuitry for collecting, processing, and sharing the pressure sensor measurements collected by the pressure sensor 210. A filling material 214 is disposed on part of the surface of the PCB 220 and on the surface of the electronic components, including the sensing or active surface of the pressure sensor 210. A multilayer coating 240 with alternating layers of ceramic and polymer is disposed on the outer surface of the sensing system 200, including on a surface of the filling material 214 and the PCB 220.

Figure 3A:
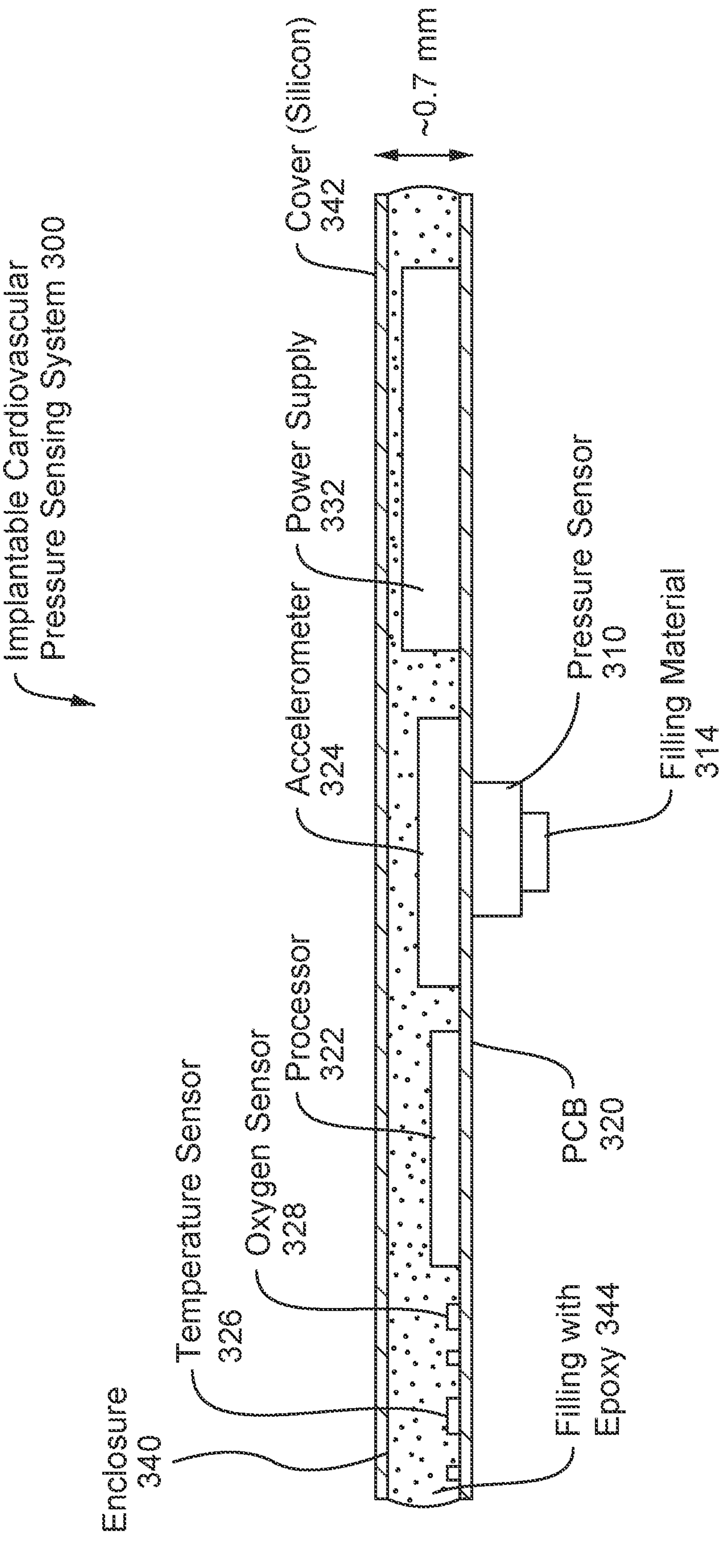
FIG. 3A illustrates a third version of implantable cardiovascular pressure sensing system with a centrally located pressure sensor designed to be near or in contact to an external surface of a blood vessel.
Figure 3B:
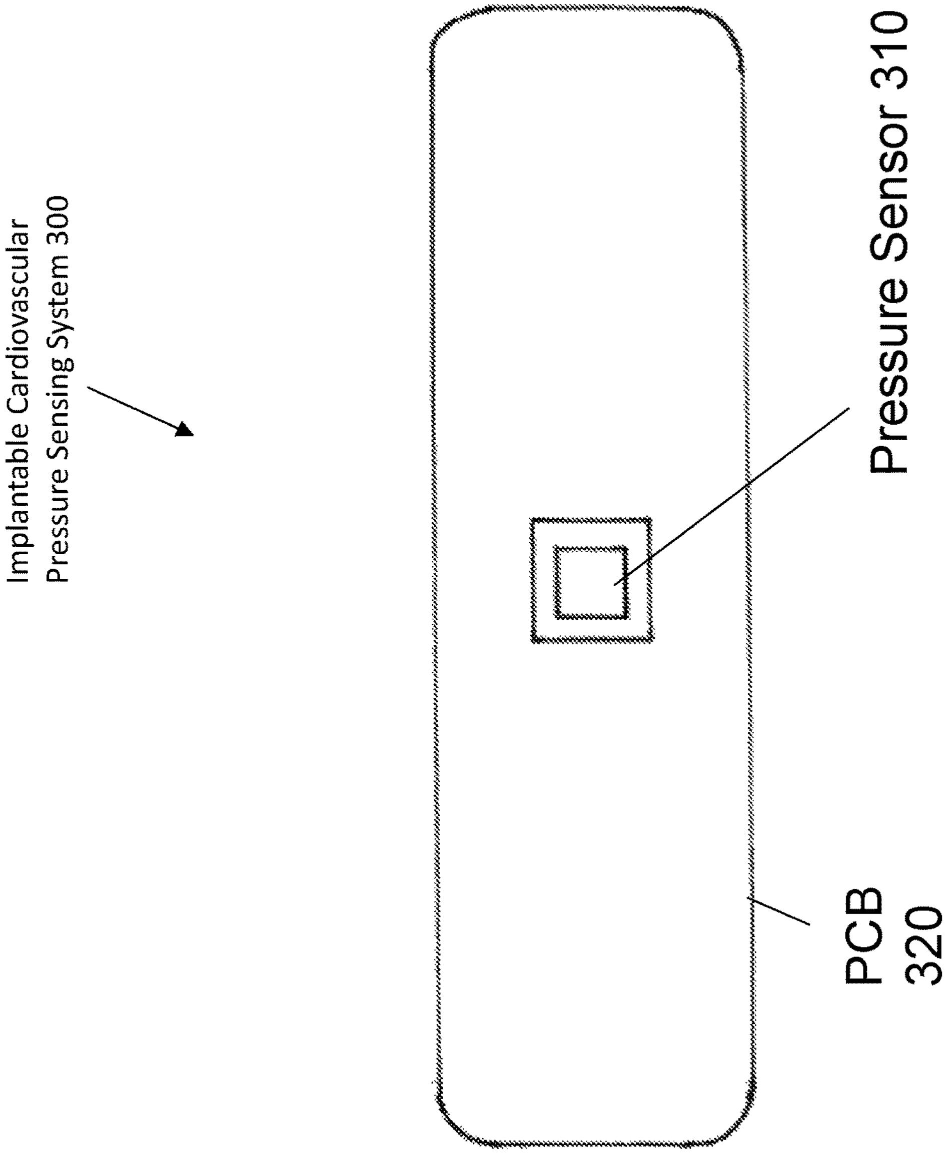
FIG. 3B illustrates an inferior view of the implantable cardiovascular pressure sensing system illustrated in FIG. 3A.
Figure 3C:
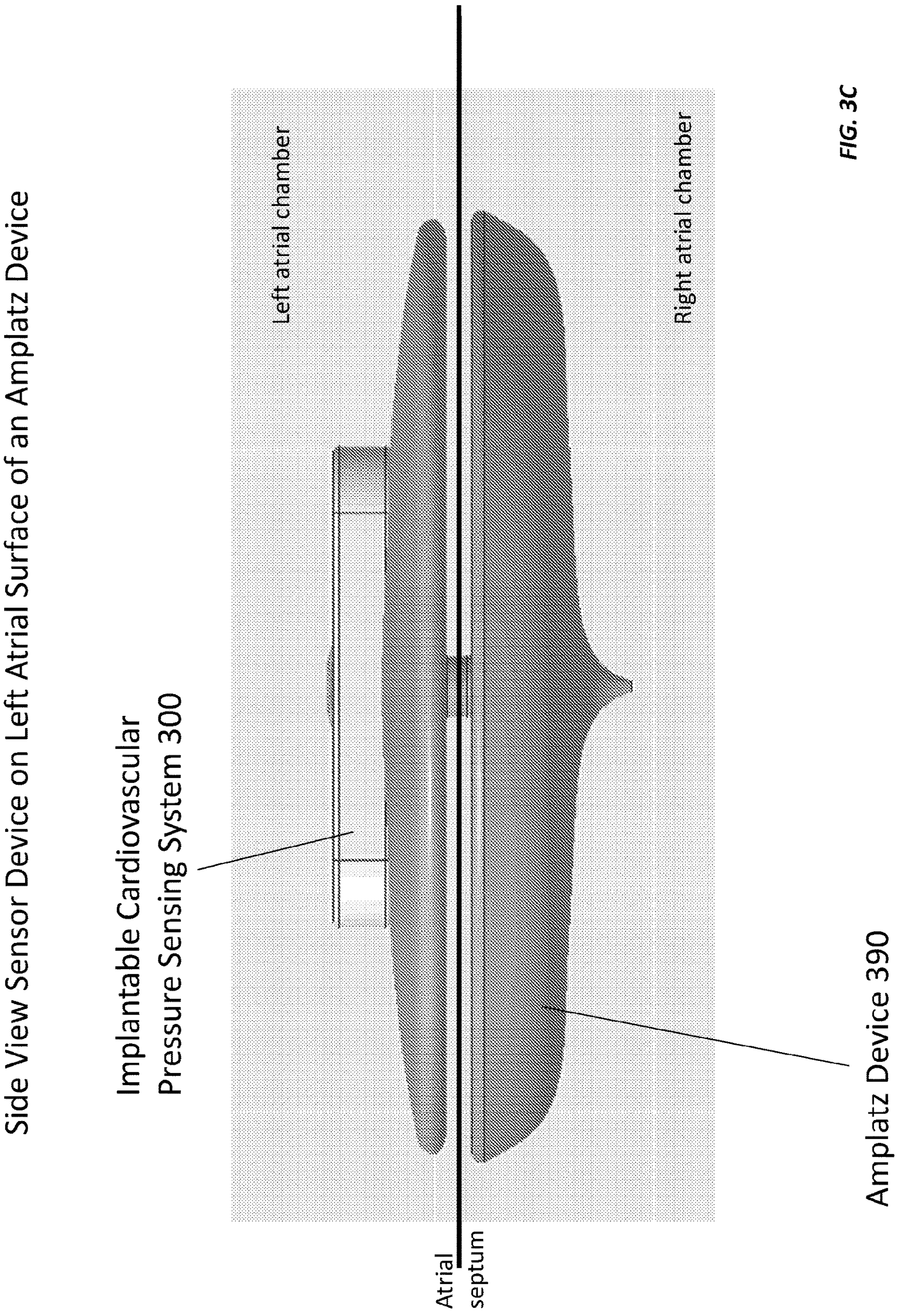
FIG. 3C illustrates implantation of the implantable cardiovascular pressure sensing system in the left atrium of the heart to measure LA pressure for the management of CHF. The sensor system is incorporated on an Amplatz occluding device placed across the atrial septum so that the sensor device is on the left atrial side of the septum.
Figure 3D:
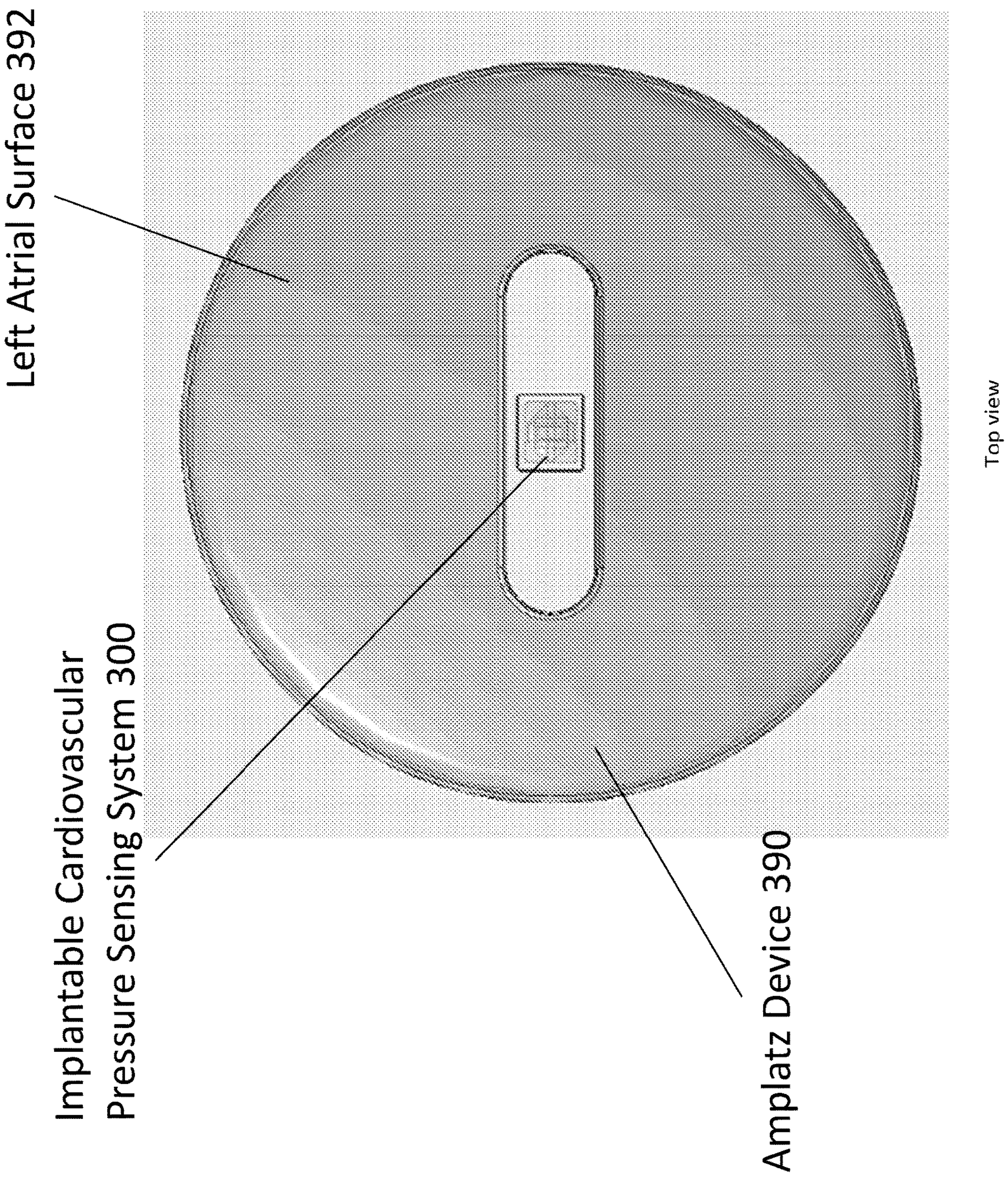
FIG. 3D shows a view of the implantable cardiovascular pressure sensing system and the left atrial side of the Amplatz occluding device of FIG. 3C.

Amplatzer Septal Occluder with Integrated Cardiovascular Pressure Sensing System FIGS. 3A-3D illustrate an alternative implantable cardiovascular pressure sensing system 300 (sensing system 300, for short) with a form factor tailored to different cardiovascular applications. FIGS. 3A and 3B show profile and plan views of the sensing system 300 by itself, and FIGS. 3C and 3D show profile and plan views of the sensing system 300 affixed to the left atrial surface 392 of an Amplatz device, also called an Amplatzer septal occluder 390.

The sensing system 300 includes a pressure sensor 310 on one side of a PCB 320 and a processor 322, accelerometer 324, temperature sensor 326, oxygen sensor 328, and power supply 332 on the other side of the PCB 320. The processor 322 is integrated with a transceiver and coupled to an antenna (not visible in these views) for exchanging data and other signals with an external device. The electronic components are contained within an enclosure 340 that is coated with a multi-layer ceramic/polymer coating as described above and filled with epoxy 344, which can have a thickness of a few microns to about 1 mm, and covered with a silicon cover 342, which can also have a thickness of a few microns to about 1 mm. Filling material 314 is disposed on the surface of the pressure sensor 310 where the sensing elements are disposed. The filling material is not disposed on the PCB 320 or other electronic components.

Figure 4A:
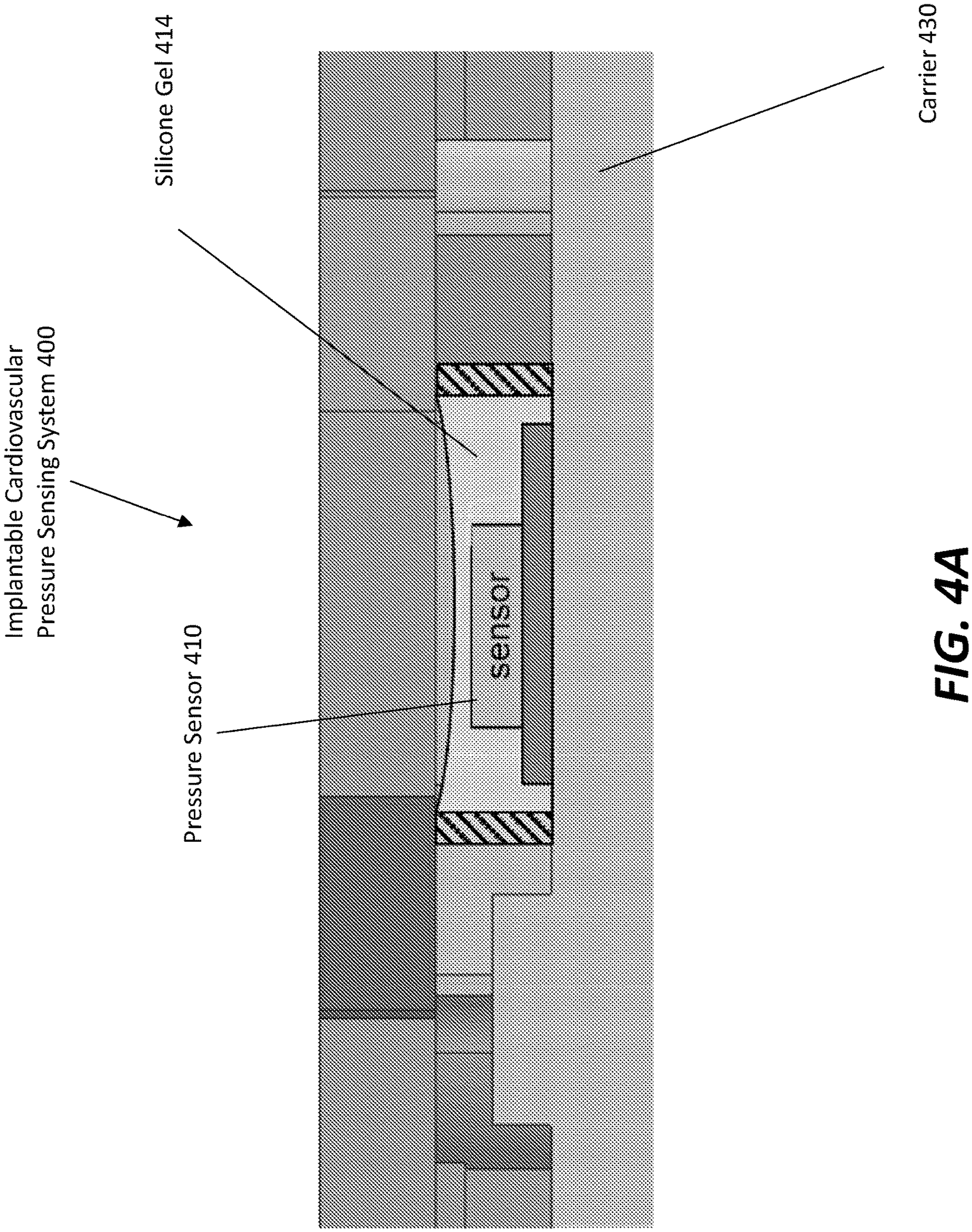
FIG. 4A illustrates a cross-section view of a fourth version of implantable cardiovascular pressure sensing system where the silicone gel is applied on top of the pressure sensor.

FIG. 4A shows an example of the implantable cardiovascular pressure sensing system 400 with a capacitive pressure sensor 410. The capacitive pressure sensor 410 is covered in silicone gel 414 and sits on a carrier 430. In operation, the capacitive pressure sensor 410 measures pressure using the change in distance between two conductive plates. The capacitance across the two conductive plates changes with the distance between the two conductive plates. The change in capacitance can be measured by read-out electronics and transmitted to the sensing system's processor (e.g., an ASIC). The pressure sensor 410 is kept isolated from blood by the outer coating on the sensing system described above. The coating prevents or substantially reduces corrosion of the pressure sensor 410.

Sensing System Electronic Architecture

Each of the implantable cardiovascular pressure sensing systems 100, 200, 300, and 400 described above includes several electronic components, including a pressure sensor, a microcontroller or processor (e.g., an application-specific integrated circuit (ASIC)), a transceiver, an accelerometer, an optional oxygen sensor, an optional temperature sensor, an antenna, and a rechargeable battery or other rechargeable power supply. The electronic components are electrically coupled to each other via the PCB upon which they are disposed and configured to operate autonomously and continually while implanted into a subject. Unless explicitly noted otherwise, each of these sensing systems 100, 200, 300, and 400 may include electronic components and operate as described below.

Together, the processor and sensors, including the pressure sensor, accelerometer, optional temperature sensor, and optional oxygen sensor, make automatic measurements at regular intervals, providing a nearly constant, continuous data flow without patient compliance or intervention. In operation, the pressure sensor measures BP in an artery or other blood vessel or vascular chamber. At the same time, the accelerometer measures the subject's motion. The processor can either store and report both the BP and motion measurements or use the motion measurements to identify, quantify, and remove motion artefacts from the BP measurements and to reported the processed BP data. The process for identification, quantification, and removal of motion artefacts is based on a combination of digital signal processing techniques and artificial intelligence.

The multilayer coating allows the entire sensing system to be small and reduces sensor drift. For instance, the sensing system's small size and shape enables the sensing system to be placed on an artery or to be shaped specifically to fit a particular structure. For instance, the sensing system 300 is roughly longitudinal in shape to fit on top of long tubular structure (artery) or to fit in the left atrium on an Amplatz device. Sensing systems of other shapes and sizes are also possible, for example, to fit within the heart.

The pressure sensor measures a fluid pressure, for example, BP in an artery. The pressure sensor may have a length of about 0.3 mm to about 1 mm (e.g., about 0.6 mm), a width of about 0.1 mm to about 1.5 mm (e.g., about 0.3 mm), and a height of 0.05 mm to about 0.4 mm (e.g., about 0.2 mm). The pressure sensor may have an accuracy of about 0.075 mm Hg to about 0.75 mm Hg. Preferably, the pressure sensor's drift over a three-month period is smaller than the pressure sensor's accuracy. Preferably, the power consumption of the pressure sensor is less than about 200 μW (100 μA) at its peak current consumption during measurement acquisition.

The pressure sensor in the sensing system may be a microelectromechanical sensor that is capacitive or piezoelectric. The pressure sensor can measure pressure in the range of 0 to about 40 or 50 mm Hg or in the range of about 40 mm Hg to about 250 mm Hg, depending on whether the sensing system is to be implanted in the heart (e.g., in the left atrium) or in or on a blood vessel, respectively. Measured blood pressures can range as high as 220 mm Hg for someone with high blood pressure or hypertension.

The pressure sensor may be a capacitive pressure sensor (also called a transducer). A capacitive pressure sensor measures pressure by detecting changes in electrical capacitance caused by the movement of a diaphragm between capacitor plates. The capacitive pressure sensor offers many advantages. The capacitive pressure sensor has higher accuracy and a lower total error band than some other pressure sensors. Moreover, the capacitive pressure sensor has a low power consumption since there is no DC current flowing through the sensor elements. Thus, the cardiovascular pressure sensing system may operate using very little power with only a small bias to the circuit.

The capacitive pressure sensor may provide very high accuracy and long-term stability. Additionally, the capacitive pressure sensor is tolerant to overpressure so that it may be safely implanted in a subject without fear of the sensor being compromised. The MEMS capacitive pressure sensor may have a lifetime of up to about 20 years.

The pressure sensor may alternatively be a piezoelectric pressure sensor. A piezoelectric pressure sensor includes a piezoelectric element that creates a difference in resistance or electrical charge when a cardiovascular pressure applies mechanical stress to the piezoelectric element. The pressure sensor measures the voltage across the piezoelectric element generated by the applied pressure to determine the amount of applied pressure. The voltage across the piezoelectric element may be measured by a Wheatstone bridge configuration, which is two piezoelectric resistors and two conventional resistors.

The device can take pressure measurements continually or intermittently at a variety of logging intervals, sampling intervals, and sampling frequency. The sensing system may be configured (e.g., using the pressure sensor and ASIC described below) to acquire pressure measurements at defined logging intervals. Logging intervals define the period of time between pressure measurement logging events when the pressure sensor is not acquiring data. The pressure sensor may be configured for logging intervals of about every 5 minutes (mins.) to about every 48 hours (hrs.) (e.g., every 5 mins., 10 mins., 15 mins, 20 mins, 40 mins, 1 hr., 2 hrs., 5 hrs., 10 hrs., 24 hrs., or 48 hrs.). Within each logging interval, the pressure sensor may be configured to acquire multiple pressure measurements at defined sampling intervals and sampling rates.

Sampling intervals are programmable and define the length of time of pressure measurements within a logging event. The sampling interval may be about 1 second (sec.) to about 10 mins. (e.g., 1 sec., 2 secs., 3 secs., 4 secs., 5 secs., 10 secs., 20 secs., 30 secs., 1 min., 2 mins., 5 mins., or 10 mins.). During the sampling interval, the pressure sensor's sampling frequency may be about 1 measurement per second (Hz) to about 500 Hz (e.g., 1 Hz, 2 Hz, 5 Hz, 10 Hz, 20 Hz, 50 Hz, 90 Hz, 100 Hz, 200 Hz, 300 Hz, or 500 Hz).

The sensing system can measure up to 90 data points per second when taking a programmed interval reading. The sensing system's processor or an external processor averages the data points. The ability to get 90 data points per second means that the sensing system can capture and present the pressures over an entire cardiac cycle. This means that unlike conventional measures of blood pressure (e.g., using a blood pressure cuff or wearable sensor), which measure only systolic and diastolic pressure, the sensing system measures waveform pressure data throughout the complete cardiac cycle. Waveform BP data for instance will measure systolic pressure, diastolic pressure, pulse pressure, and dicrotic notch—all richer data that is clinically relevant.

As an example, the pressure sensor may monitor pressure within the cardiovascular system at logging intervals of 10 minutes, with every sampling interval being a period of 10 seconds to 30 seconds of continuous pressure sensing, e.g., at a frequency of 90 Hz. As another example, the capacitive pressure sensor may collect 1 to 90 measurements about every 10 minutes to about every 24 hours. As another example, the pressure sensor may be configured to acquire beat-to-beat measurements, where the time interval between heart beats is measured. In this example, the pressure sensor may be configured to acquire measurements with sampling intervals of about 1 second to 2 seconds at frequencies of about 90 Hz.

The sensing system may prevent or substantially reduce drift caused by fibrotic buildup by exposing sense and reference capacitors to the same environment. A conventional MEMS capacitive pressure sensor element includes two sense capacitors and two reference capacitors. In a conventional MEMS capacitive pressure sensor, the reference capacitors are not sensitive to pressure variations. A conventional MEMS capacitive pressure sensor's long-term stability may be determined by the aging of the sensing elements and thereby the drift in its measurement accuracy over time. In contrast, the MEMS capacitive pressure sensor in the cardiovascular pressure sensing system may include at least one sense capacitor and reference capacitor that are exposed to the same environment. The sense and reference capacitors are exposed to the same conditions and stimuli that cause sensor aging and long-term drift. Since the sense and reference capacitors are exposed to the same conditions and are manufactured using the same materials and procedures, they also age with the same rate. Therefore, the MEMS capacitive pressure sensor's long-term drift effect may be reduced so that it may provide accurate measurements with long-term stability.

Figure 4B:
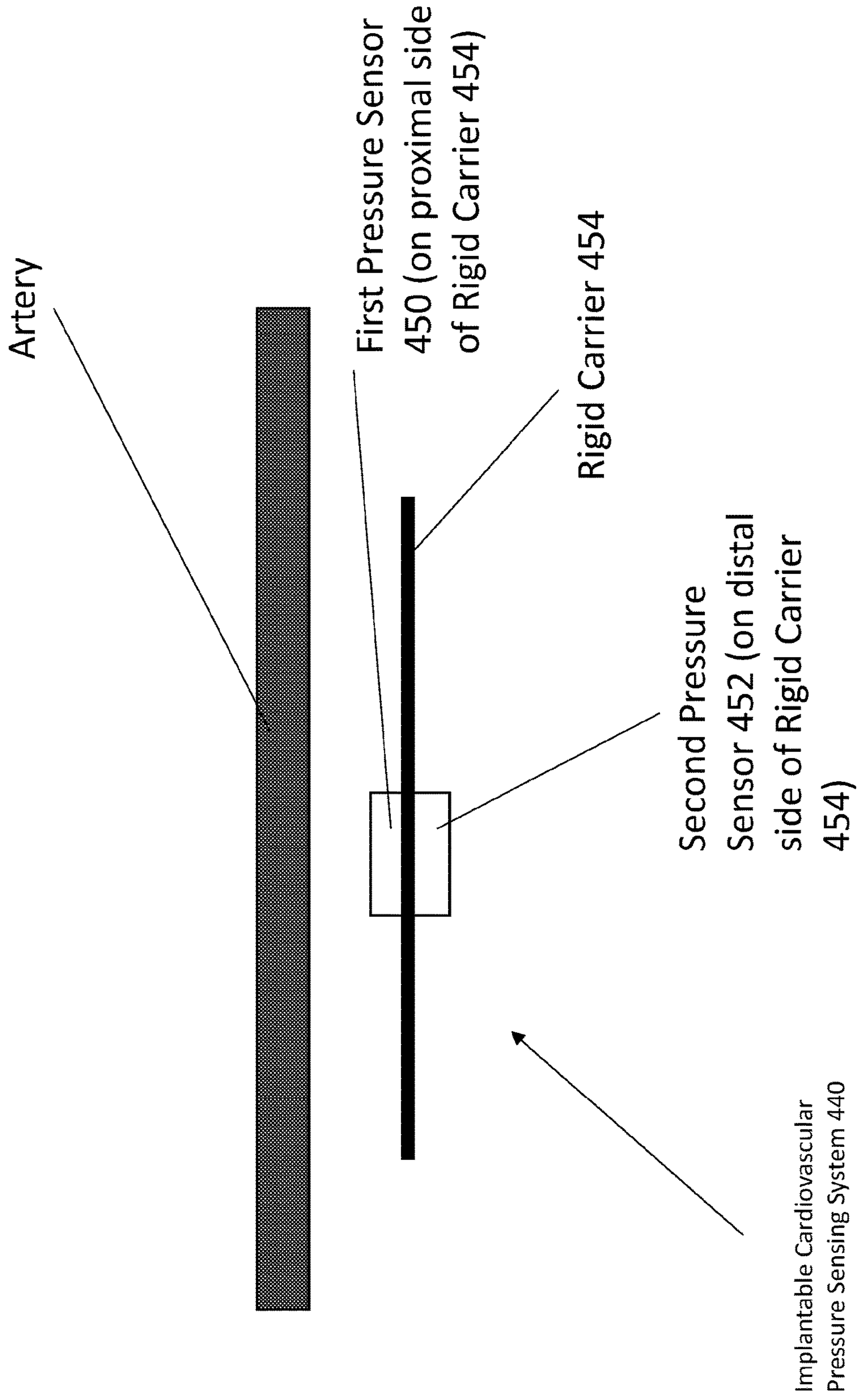
FIG. 4B shows an implantable cardiovascular pressure sensing system with a second pressure sensor.

FIG. 4B shows an implantable cardiovascular pressure sensing system 440 with both a first pressure sensor 450 for measuring blood pressure and a second pressure sensor 452 for measuring other internal pressure. The first pressure sensor 450 and second pressure sensor 452 are on opposite sides of a rigid carrier 454: the first pressure sensor 450 is mounted on the side of the rigid carrier 530 that will be proximal to the blood vessel once the sensing system 440 has been implanted, and the second pressure sensor 452 is on the distal side. Because the second pressure sensor 452 is positioned in a different location than the first pressure sensor 450, it is exposed to a different pressure than the first pressure sensor 450. This second pressure sensor 452 may help to compensate for pressure variations not related to blood pressure variations, e.g., patient position and posture or variations in body fluid distribution.

Figure 4C:
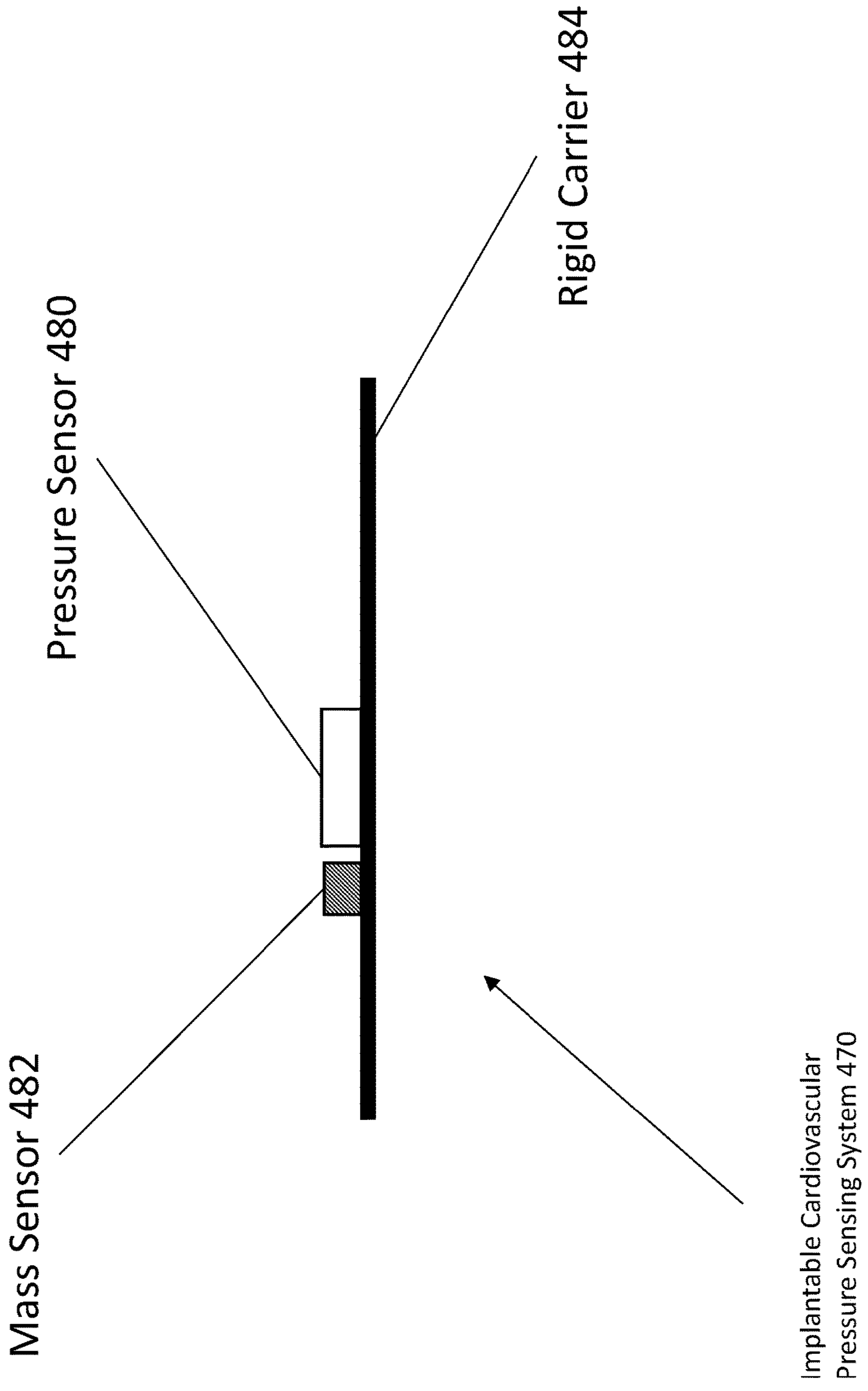
FIG. 4C shows an implantable cardiovascular pressure sensing system with a mass sensor for compensating pressure sensor drift.

FIG. 4C shows an implantable cardiovascular pressure sensing system 470 with a pressure sensor 480 and a mass sensor 482 on a rigid carrier 484 (e.g., a PCB). The mass sensor 482 detects and measures the amount of fibrous tissue deposited on the surface of the pressure sensor 480 so that the pressure sensor 480 can be automatically calibrated according to the amount of buildup. In this example, the mass sensor 482 may be positioned adjacent to the pressure sensor 480 assembly on the PCB, such that the mass sensor 482 is adapted to monitor the mass of fibrous tissue deposited on the outer surface of the sensing system 470. This mass sensor 482 aids calibration of the pressure sensor 480. The mass sensor 482 may be a quartz microbalance, a surface acoustic wave sensor, or any other type of sensor that monitors the magnitude of the mass of deposits that collect on the outer surface of the sensing system, or the surface of an additional biocompatible coating that may be applied in order to minimize post-operative inflammation. Readings of the mass sensor 482 may be processed by on-board circuitry to compute a compensation to the raw pressure measurements. The corrected pressure measurements may then be transmitted to an external sensing system. Alternatively, the sensing system 470 may send data from the mass sensor 482 along with the raw pressure measurements to the external sensing system so that the pressure data may be processed using the external sensing system. If there are calibration issues due to fibrotic tissue buildup, the pressure sensor 480 can be zeroed against a reference sensing system of the patient's physician's choice at any time either at home or in the physician office.

The sensing system may include other sensors, including a temperature sensor and/or an oxygen sensor. An oxygen sensor may be used to measure blood oxygen levels in the subject. Blood oxygen measurements may be used with absolute relative pressure measurements to calculate fundamental hemodynamic index calculations. The sensing system may also include a temperature sensor.

The sensing system may include an accelerometer. The accelerometer may be used to detect and possibly compensate motion artefacts. In addition to this, the accelerometer may also compensate for pressure variations due to variations of posture (e.g., standing, lying, lifting of arm). Compensation of artefacts and variations can be done by either discarding the pressure data during artefacts and variations, or by correcting for the artefact or variation based on patterns that have been learned from training data. Furthermore, the accelerometer may also be used for saving energy during certain periods of the day, e.g., when the patient is lying down and sleeping.

The sensing system includes an ASIC. The ASIC receives signals from the sensors on the sensing system and acts as the sensing system's controller. The ASIC may include a pressure to data converter function that processes signals from the one or more pressure sensors and data processing functions to process the data (e.g., time-averaging). The ASIC may include one or more forms of memory. For example, the ASIC may include volatile memory (e.g., RAM) that is used for control and processing functions. The ASIC may also perform timer and sequencer functions. In another example, the ASIC may have a flash memory that is used to perform some data processing. For example, the flash memory may be used to perform signal averaging of sensor data received from the pressure sensor. The ASIC may also include a power controller to manage electrical power usage by the sensing system. For example, the ASIC may determine the charge state of a rechargeable battery in the sensing system that provides electrical power to the electrical components in the sensing system and indicate to the patient or healthcare provider when the battery needs to be recharged (e.g., by sending a wireless notification to an external device). The ASIC may also manage wireless communication components in the sensing system. For example, the ASIC may adjust electrical characteristics of an antenna circuit in order to maximize wireless coupling efficiency. As an example, the ASIC may have dimensions of 1.1 mm by 1.1 mm by 0.1 mm. Alternatively, the functions of the ASIC may be implemented with a microcontroller and additional discrete components.

The ASIC may provide autonomous operation of the sensing system. Autonomous operation means that the patient does not need to manual intervene in order for the sensing system to operate. In this way, the sensing system is not plagued by issues related to patient compliance. The ASIC may perform internal calibrations of the various sensors in the sensing system. For example, the ASIC may perform internal calibration of the pressure sensor using data on the amount of fibrous tissue buildup measured by the mass sensor. The ASIC may also receive calibration signals from an external device via the antenna and trans-receiver described below. As another example, the ASIC may be programmed to activate the pressure sensor and/or other sensors in the sensing system according to desired logging intervals, sampling intervals, and sampling frequencies. Alternatively, the functions of the ASIC may be implemented with a microcontroller and additional discrete components.

The sensing system may include a trans-receiver coupled to the ASIC and to the antenna. The trans-receiver may transmit and receive data to and from an external device. The trans-receiver may also receive power from the external device to charge the sensing system's power source. The trans-receiver may transmit and receive data and power over a range of about 2 meters to 20 mm (e.g., 2 meters, 1.5 meters, 1 meter, 50 cm, 10 cm, 1 cm, 50 mm, or 20 mm). The trans-receiver uses an RF frequency of about 100 kHz to 6 GHz.

The sensing system may also include another form of non-volatile memory to store sensor data. For example, the non-volatile memory may be an electrically erasable programmable read-only memory (EEPROM) disposed on the PCB. The EEPROM may receive pressure sensor data from the ASIC and store that data. The data received by the EEPROM may be signal-averaged data that was signal averaged by the ASIC. The data stored in the EEPROM may be transferred to an external device using the wireless communication components in the sensing system.

The sensing system's power source may be a rechargeable battery that is disposed on the PCB and that powers the sensing system. The rechargeable battery may be recharged wirelessly while the sensing system is implanted via the wireless communication components. The ASIC may handle power management functions to manage the rechargeable battery. For example, the battery may be a solid-state rechargeable lithium polymer battery with a cycle life of 2000-3000 cycles. With the battery recharged twice per week, this battery may have a lifetime of greater than 15 years. As an example, the battery may have a size of about 1.7 mm by 2.25 mm by 0.2 mm.

Figure 6A:
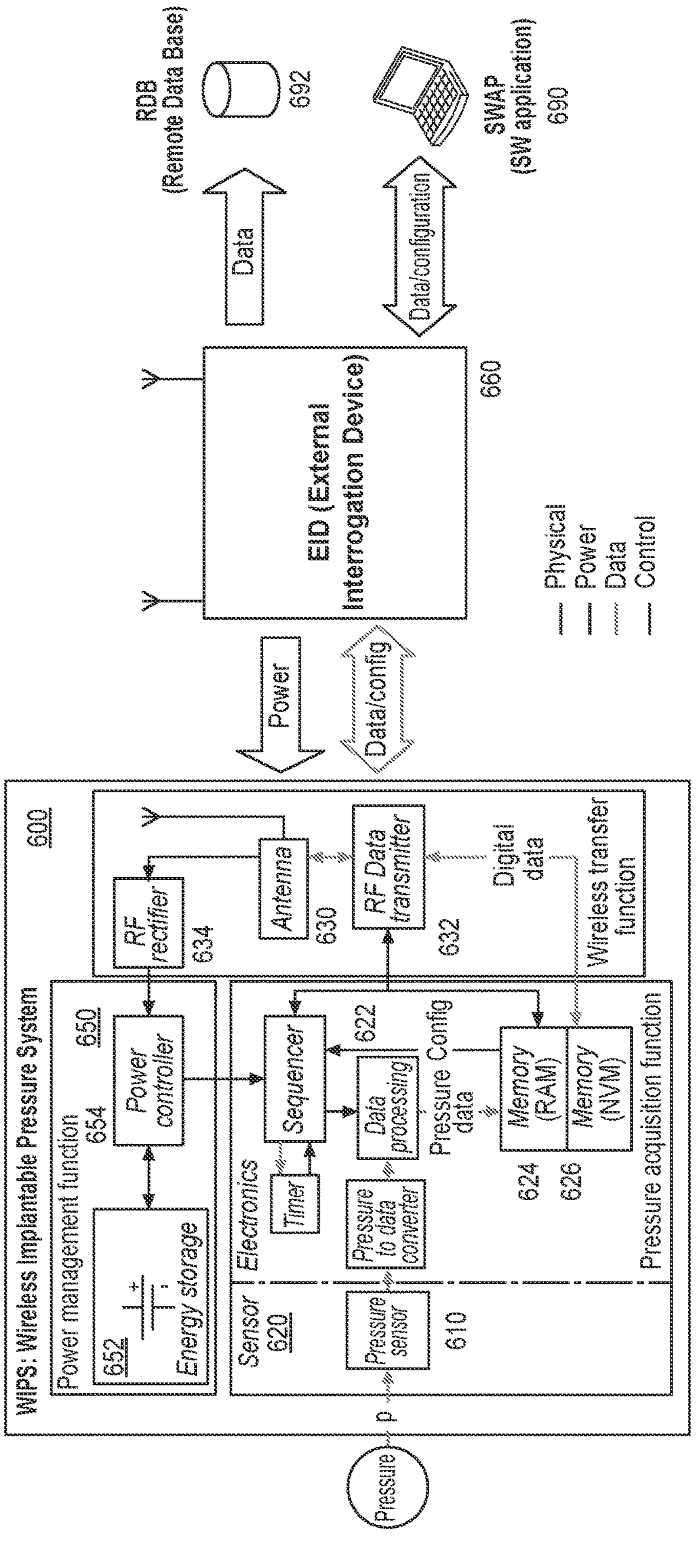
FIG. 6A is a block diagram of a first version of an implantable cardiovascular pressure sensing system interfacing with an external device.

FIG. 6A is an example block diagram of the components in a cardiovascular pressure sensing system 600 (e.g., as in FIGS. 1A, 2A, 3A, and 4) interfacing with a non-implanted external interrogation device (EID) 660, also known as an external device 660, which interfaces in turn with a remote database 692 and/or a software application 690 executing on a computer. The sensing system 600 includes a power management function 650, which includes an energy storage component 652 (e.g., a rechargeable battery) and a power controller 654. The sensing system 600 also includes the pressure sensor 610 and electronic components to receive pressure sensor measurements. The electronic components, which may be part of an ASIC 620, include a timer and sequencer used to set measurement frequencies and duty cycles, a pressure-to-data converter to convert pressure measurements to digital data, and a data processor 622. The sensing system in FIG. 6A also includes at least two forms of memory (e.g., random access memory (RAM) 624 and non-volatile memory (NVM) 626). The RAM 624 may be used for processing data from the sensors. The NVM 626 may store sensor data for a period of time (e.g., 1 day, 2 days, 5 days, or 10 days) before the data is transmitted to the EID 660.

The sensing system in FIG. 6A also includes wireless communication components, including an antenna 630, an RF data transmitter 632, and an RF rectifier 634. The wireless communication components are used to transmit data and operation settings to the EID 660, to receive signals from the EID 660 to change operation settings, and to receive power wirelessly to recharge the energy storage component 652. Depending on the application, communication and wireless power transfer may operate in the near-field regime (e.g., 10 kHz to 100 MHz), or in the mid-field or far-field regime (e.g., 100 MHz to 6 GHz). For the near-field regime, typically a magnetic coil antenna is used, whereas an electric patch antenna is typically used for the mid-field or far-field regime. The EID 660 may display and/or analyze the data using the software application (SWAP) 690. The EID 660 may also upload the data to a remote database 692 where it may be stored and may be accessible by healthcare professionals and/or the subject.

Figure 6B:
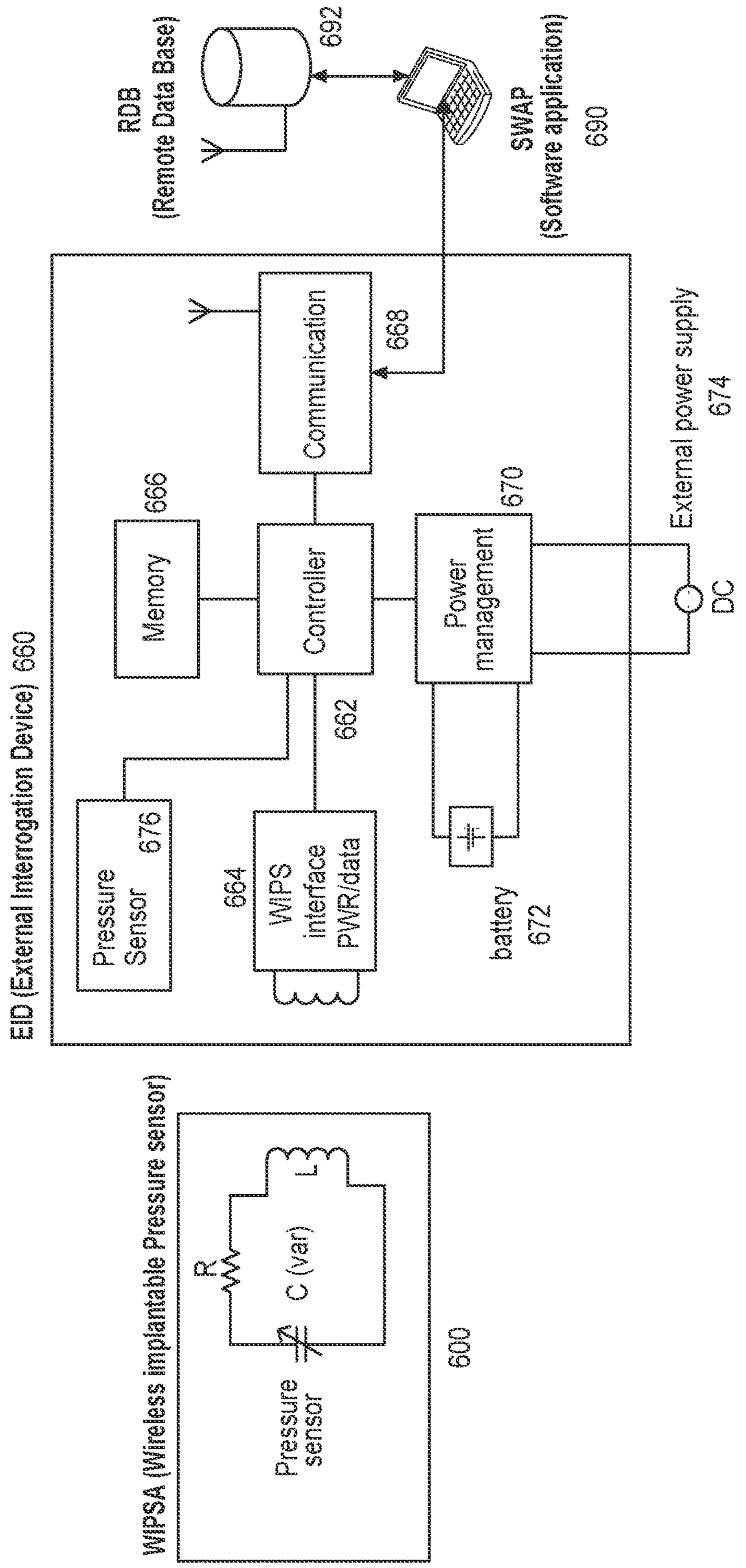
FIG. 6B is a block diagram of a second version of an implantable cardiovascular pressure sensing system interfacing with an external device.

FIG. 6B shows another block diagram of components in a cardiovascular pressure sensing system 600 and the EID 660. The sensing system 600 in FIG. 6B includes a capacitive pressure sensor and a wireless communication components or chip to transmit data acquired by the sensing system's sensors. The EID 660 includes a wireless communication interface 664 to send and receive signals from the sensing system 600. The EID 660 may also include a processor or controller 662, memory 666, and power management 670 as well as an optional atmospheric pressure sensor 676 for measuring ambient or atmospheric pressure outside the subject's body. The EID's processor 662 can use these atmospheric pressure measurements to compensate or correct for fluctuations in BP measured by the sensing system 600 caused by fluctuations in atmospheric pressure.

The EID may include a battery 672 and/or an external power supply 674. The EID may optionally include a second communication chip 668 to upload the data to the other computer 690 and/or a remote database 692. Alternatively, the EID 660 may include a single communication chip that communicates with both the sensing system and other computers.

Figure 6C:
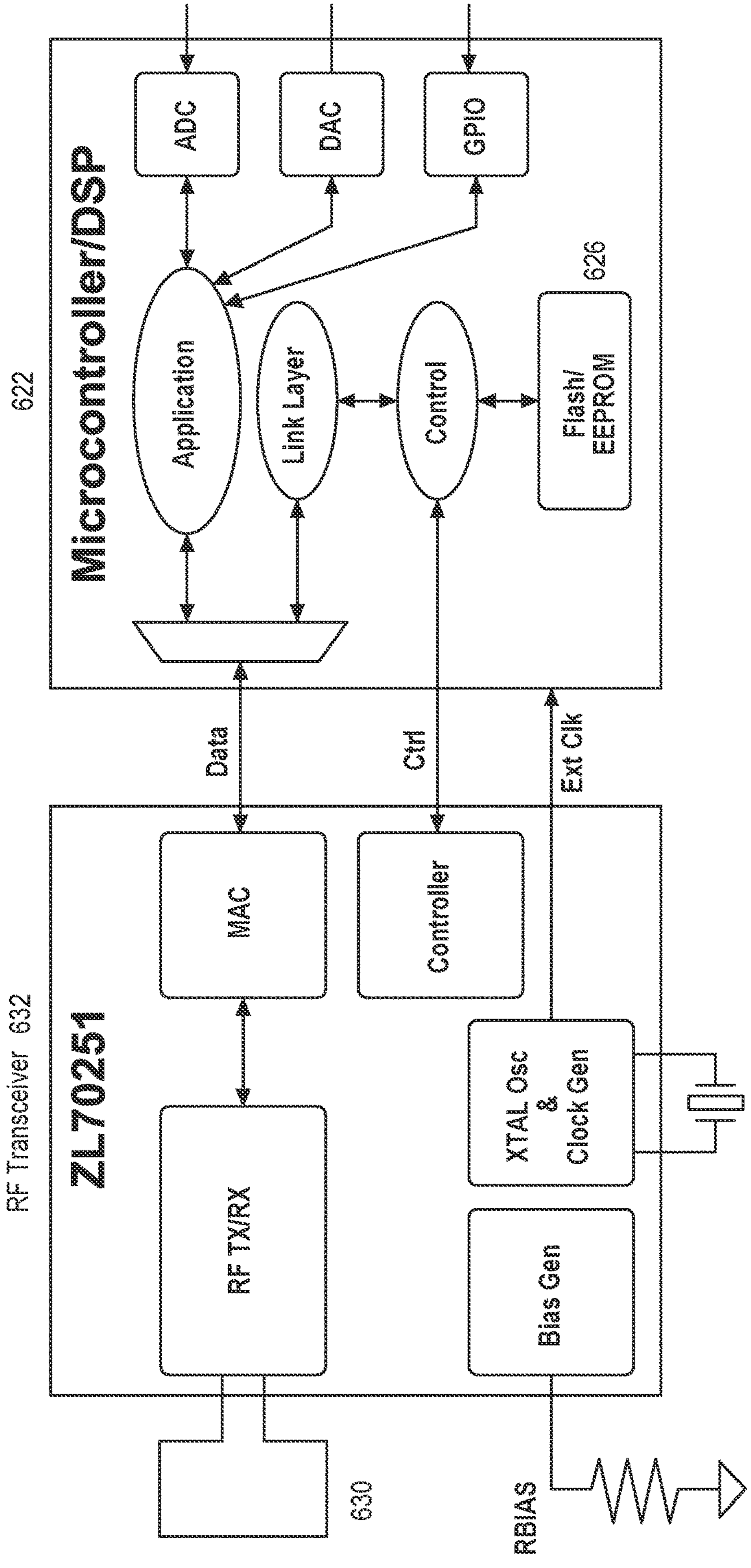
FIG. 6C is a block diagram of a transceiver and microcontroller in an implantable cardiovascular pressure sensing system.

FIG. 6C is a block diagram of a radio-frequency (RF) transceiver 632 and microcontroller 622 suitable for use in any of the implantable cardiovascular pressure sensing systems disclosed here. The wireless communication components in the sensing system transmit signals to and receive signals from one or more external devices. The wireless communication components may perform wireless telemetry. For example, the wireless communication components may transmit sensor data to an external device. As another example, the wireless communication components may receive signals from an external device to configure the sensing system's settings (e.g., pressure measurement frequency and duration). As another example, the wireless communication components may provide wireless recharging to the sensing system's rechargeable battery.

Figure 7:
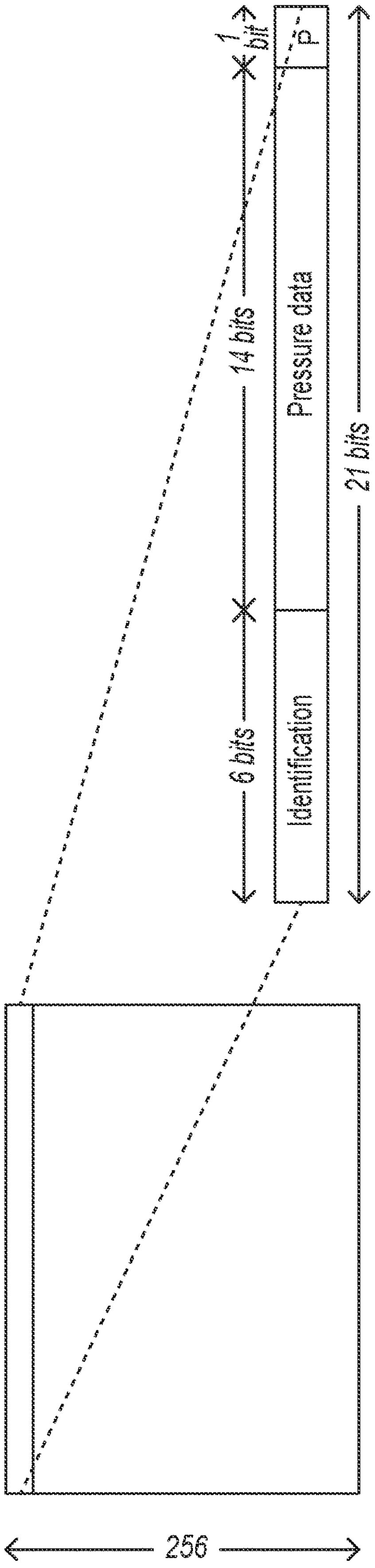
FIG. 7 illustrates a pressure data size and encoding scheme for an implantable cardiovascular pressure sensing system.

FIG. 7 illustrates an example of the pressure data size and encoding scheme for the pressure sensing system so that the data may be wirelessly transmitted to the EID. The wireless communication components are disposed in the cavity of the sensing system housing and may include an antenna, a radio-frequency (RF) data transmitter, and an RF rectifier. In an example, the wireless communication components include a transceiver. The transceiver may operate using low transmit and receive currents of less than 2.4 mA and a low supply voltage of about 1.2 V to about 1.9 V. The transceiver may use an RF frequency of about 779 MHz to 965 MHz (e.g., 779-787 MHz, 868 MHz, and/or 915 MHz). The transceiver may have a high data rate (e.g., 186 kbit/s raw), even through up to 1 meter of body tissue or up to 10 meters through air.

Communication with the external device may be encoded and each data transfer may be preceded and ended with a handshake. An alert may be included whenever data transfer from the implanted sensing system to the external device is corrupted. The external device can execute user-originated commands to execute data transfer from the implanted sensing system to the external device. The data transferred to the external device may undergo additional data processing at the external device.

The EID or another computer may process the raw data measured by the pressure sensing system, including calibration, compensation, filtering, conversion to pressure units, and/or visualization. The EID may have an absolute pressure sensor (e.g., pressure sensor 676 in FIG. 6B), in order to compensate for variations in ambient atmospheric pressure (e.g., due to altitude or weather conditions), to which the implanted pressure sensing system is exposed. The EID may generate a parametric blood pressure model for the subject using the pressure data. For example, the external device may smooth a data set to create an approximating function that captures patterns in the data while reducing noise. In smoothing, the data points of a data set are modified so individual points higher than the adjacent points (presumably because of noise) are reduced, and points that are lower than the adjacent points are increased leading to a smoother signal. The external device may be 4G and WiFi compatible so that it can upload data to a cloud-based repository platform where healthcare professionals may aggregate and analyze the data and/or share the data with other healthcare professionals.

Pressure Sensor Drift

Pressure sensor drift is a common problem with implanted sensors that can lead to inaccurate and unreliable pressure measurements, and eventually sensor failure. Drift is the gradual decrease in accuracy of a sensor's measurements. For example, drift may manifest as a gradual increase or decrease in a baseline pressure measurement. Drift can be caused by several factors, including the natural degradation of the pressure sensor components, fluctuations in environment, and exposure to water and other chemicals. Conventional pressure sensor drift for a conventional pressure sensor is about 2 mm Hg per year.

For implanted pressure sensors, drift can be an especially big problem because the accumulation of the host's tissue (e.g., fibrotic tissue as a result of the foreign body response) on the sensing elements can cause large amounts of drift. Also, implanted pressure sensors are exposed to liquid environments thereby risking liquid (e.g., water or other biological fluid) infiltration into the sensor, which can cause substantial drift, corrosion of sensor elements, and sensor failure.

Conventional pressure sensors should be calibrated regularly to counteract the effects of drift, but implanted pressure sensors are difficult to calibrate. Sensor drift and calibration are two areas generally associated with sensor failure over time and may be the root cause of conventional implanted sensing system failures. Calibration of conventional pressure sensors involves subjecting the pressure sensor to at least two different known pressures, and preferably at least five known pressures, to create a pressure calibration curve. The calibration curve can be used to interpolate to determine experimental pressure measurements.

Conventional calibration is extremely difficult or impossible when the pressure sensor is implanted. Calibration is a complex issue when the pressure sensor is in an environment of fibrous encapsulation. To calibrate an implanted pressure sensor using conventional means, the sensor may need to be explanted, a costly and painful process for the host patient. Even if the calibration of the pressure sensor can be performed in situ, the process still requires a high level of patient involvement and compliance, creating a high risk of sensor failure due to patient non-compliance. Therefore, there is a need for implantable pressure sensors that don't need to be calibrated as often and that have calibration mechanisms that don't require substantial patient involvement.

The inventive sensor system has been designed to minimize the occurrence and effect of sensor drift. The inventive methods for reducing sensor drift are described below.

FIGS. 1A, 2A, 3A, and 4 show various versions of an implantable cardiovascular pressure sensing system ("sensing system") configured to substantially reduce or prevent the sensing issues related to sensor drift and calibration of implanted pressure sensors. Each of these sensing systems may use one or more strategies to mitigate the risks of sensor drift and patient non-compliance with calibration. One strategy includes using an isolation package including a biocompatible coating that encapsulates the sensing system. Another strategy includes using a mass sensor that measures the amount of fibrous tissue deposited on the surface of the pressure sensor so that the pressure sensor can be calibrated appropriately automatically to account for the fibrous tissue. These and other strategies are described in more detail below.

The sensing systems shown in FIGS. 1A, 2A, 3A, and 4 may reduce drift as a result of the aging of the sensing elements by limiting the sensing elements interactions with water. Long term stability of the pressure sensor and drift in measurement baseline over time is affected by the aging of the sensing elements. Aging can be accelerated by the sensing elements interacting with water or other biological fluids.

The sensing systems shown in FIGS. 1A, 2A, 3A, and 4 can include isolation packaging that prevents or substantially reduces the risk of water or fluid infiltration into the sensing systems. The isolation packaging may include a filling material and a multilayer coating (also called a film) covering the sensor body. These components are described in more detail in the sections below. The filling material may be disposed on at least part of some of the electronic components including the sensing elements of the pressure sensor. The multilayer coating, which may be disposed on the filling material, may be flexible so that it transmits pressure from the environment to the filling material, which in turn transmits the pressure to the sensing elements. In this way, the multilayer coating is mechanically coupled to the sensing elements via the filling material.

The filling material may be infused with a small amount of water or other liquid (e.g., about 0.001% by weight to about 5% by weight, including 0.002%, 0.005%, 0.01%, 0.05%, 0.1%, 0.5%, 1%, or 5%) that helps stabilize drift. Additionally, the sensing systems shown in FIGS. 1A-4 may be hermetically sealed by a multilayer coating to prevent the infiltration of water or other liquids into the sensing systems. Together, the filling material and multilayer coating prevent or substantially reduce water infiltration that would otherwise cause sensor aging and drift.

The sensing systems shown in FIGS. 1A-4 may also reduce drift caused by accumulation of fibrotic tissue on the sensing system. The multilayer coating on the sensing system may also be biocompatible and thus reduce fibrotic tissue accumulation on the sensing system. The sensing system may also include a mass sensor that measures the amount of fibrotic tissue accumulated on the sensing system and automatically calibrates the pressure sensor in the sensing system based on the amount of fibrotic tissue accumulation measured. Also, the sensing system may prevent or substantially reduce drift caused by fibrotic buildup by exposing sense and reference capacitors to the same environment. These components are described in more detail below.

Multilayer Coatings for Implantable Cardiovascular Pressure Sensing Systems

The multilayer coating shown in FIGS. 1A and 2A prevents water intrusion or infiltration into the sensing system. Water infiltration may cause undesirable drift of the pressure sensor's baseline and may corrode the sensing system's components. The multilayer coating is also biocompatible to prevent or substantially reduce the accumulation of the host's fibrotic on the sensing system. Fibrotic tissue builds up on the sensing system, especially near the sensing elements, can cause substantial pressure sensor drift.

Figure 5B:
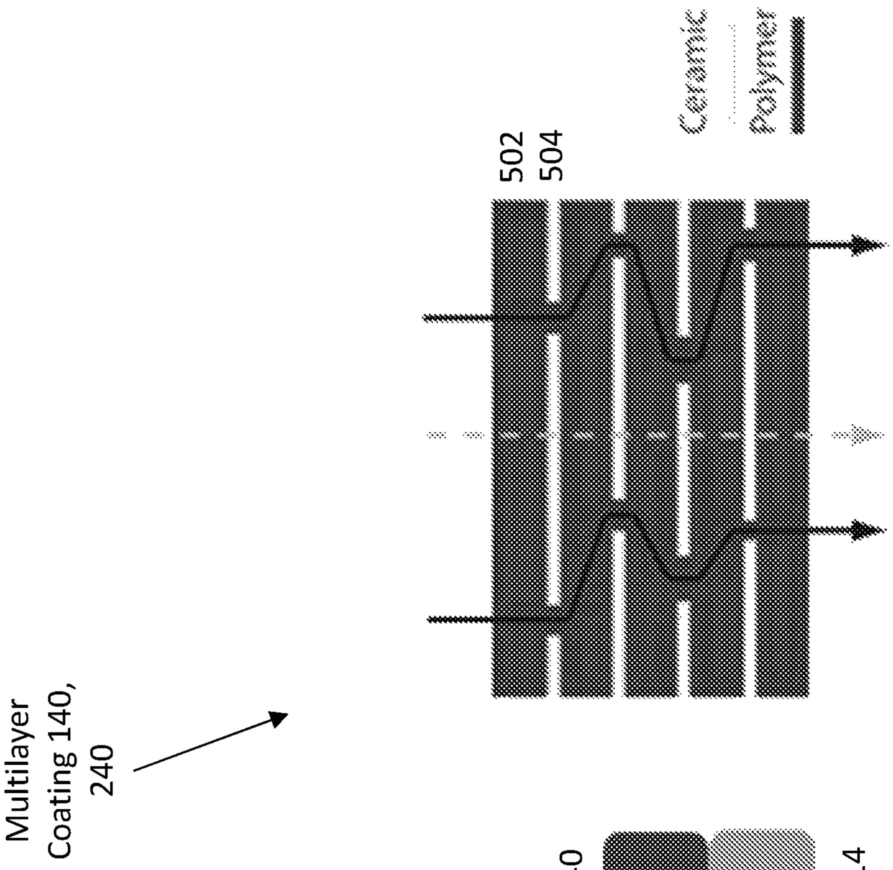
FIG. 5B illustrates a multilayer barrier coating for the cardiovascular pressure sensing system.
Figure 5A:
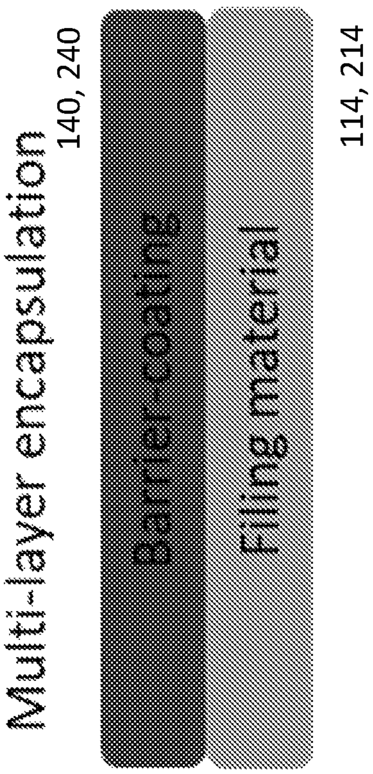
FIG. 5A illustrates a multilayer encapsulation for the cardiovascular pressure sensing system.

FIG. 5A illustrates the multilayer coating 140, 240 disposed on the filling material 114, 214. FIG. 5B illustrates alternating polymer layers 502 and ceramic layers 504 in the multilayer coating 140, 240 on the sensing system 100, 200. As explained above, the sensing system 100, 200 may include a multilayer coating 140, 240 on its outer surface. The multilayer coating 140, 240 is a biocompatible, flexible film that covers the sensing system 100, 200 and creates a hermetic seal so that biological fluids cannot interact with any of the sensing system's components. The multilayer coating 140, 240 prevents water intrusion or infiltration into the sensing system 100, 200. Water infiltration may cause undesirable drift of the pressure sensor's baseline and may corrode the sensing system's components.

FIGS. 5A and 5B show an example multilayer coating 140, 240 having layers 502, 504 of polymer (e.g., Parylene C) and ceramic (e.g., $SiO_x$). The different layers need not be made up of the same materials or thicknesses, but rather can comprise different materials or thicknesses. The total thickness of the multilayer coating 140, 240 is chosen so that it is thin and flexible enough that it will transmit pressure P exerted by in environment outside of the sensing system 100, 200 to the filling material 114, 214, which transmits the pressure to the pressure sensor 110, 210. If the multilayer coating 140, 240 is too thick, the pressure sensor's sensitivity is reduced. If the multilayer coating 140, 240 is too thin, the sensing system 100, 200 may not durable enough to be impermeable to water and the pressure sensor 110, 210 may become exposed to water, causing the pressure sensor 110, 210 to fail.

In some embodiments the total thickness of the coating is in the range of 5 μm to 1 mm (e.g., 5 μm, 10 μm, 14 μm, 20 μm, 25 μm, 50 μm, 100 μm, 150 μm, 200 μm, 500 μm or 1 mm). As an example, each layer may be about 1 μm thick, the multilayer coating may alternate between the ceramic layer and polymer layer, and the multilayer coating may have a total thickness of about 14 μm.

Conventionally, when an object is implanted into a host, the object is subjected to a series of well-defined processes characterized as the foreign body reaction that ultimately leads to fibrous encapsulation of the implanted device. The implanted object may be isolated from the body by a dense collagenous capsule as collagenous fibrotic tissue builds up on the surface of the device.

The multilayer coating on the sensing system reduces or prevents adhesion of the host's cells present in the surrounding environment, including macrophages, to the multilayer coating surface in order to reduce or prevent the host's foreign body response. If the host's cells were to adhere to the surface of the implanted sensing system, they may trigger an immune response leading to proliferation of these cells. Even when cells attach to the surface of the coating, this attachment may be reversible, with the cells retaining their round shape. The surface of the multilayer coating may also prevent or substantially reduce attachment of proteins and smaller peptides to the coating surface. Even when attachment does take place, the energy of adhesion is reduced, so that the attached protein does not undergo denaturation that may change the cell's shape. The multilayer coating may be hydrophilic to reduce adhesion of cells and proteins.

The multilayer coating may also be composed of materials that have biocompatible and/or non-toxic molecular structures. The multilayer coating formed from such chemicals may be non-toxic, especially when it is post-processed to remove all reactant chemicals, after it has been formed (e.g., polymerized in place).

The multilayer coating may also modulate the immune response by including chemicals that are slowly released from the multilayer coating over time. For example, the coating may include an inhibitory peptide for the IL-1 receptor. As another example, the multilayer coating may include an inhibitor of the cytokine TGFβ, which is widely implicated as being a central mediator of the fibrotic response. One particular example of a chemical that inhibits expression of critical cytokines is Pirfenidone having the following molecular structure:

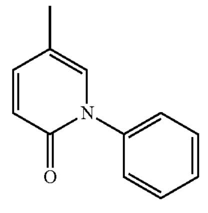

Pirfenidone is an inhibitor for TGF-β production and TGF-β stimulated collagen production, and it reduces production of TNF-α and IL-1β, and also has anti-fibrotic and anti-inflammatory properties. Another example chemical that can be incorporated into any of coatings herein to inhibit expression of cytokines is Galunisertib, a potent TGFβ receptor I (TβRI) inhibitor, having the chemical structure:

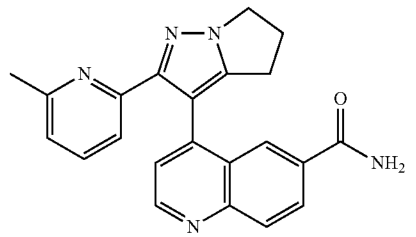 [SMILES: Cc1cccc(-c2nn3c(c2-c2ccnc4ccc(C(N)=O)cc24)CCC3)n1]

Another example chemical that can be incorporated into any of coatings herein to inhibit expression of critical cytokines is LY2109761, which is a selective TGF-β receptor type I/II (TβRI/II) dual inhibitor, having the chemical structure:

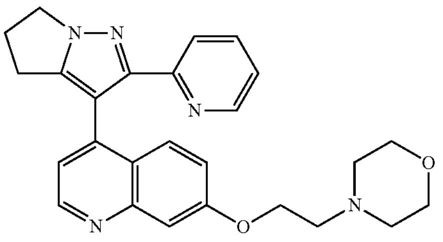 [SMILES: c1ccc(-c2nn3c(c2-c2ccnc4cc(OCCN5CCOCC5)ccc24)CCC3)nc1]

Other pharmaceuticals can also be incorporated into the multilayer coating, including but not limited to heparin, both low and medium molecular weight to control fibrosis and provide anticlotting functionality; steroids; anti-inflammatories such as dexamethasone, or other corticosteroids; Cox 1- and Cox-2 inhibitors to control inflammation: pressure reducing agents such as beta blockers and carbonic anhydrase inhibitors. The steroid prednisolone may also be incorporated.

Since the total weight of the coatings herein is generally in the range of 4-6×$10^{-4}$ g, a 10% loading of a corticosteroid (e.g., Prednisolone) provides an average life of 500 hours.

The coatings herein may be hydrophilic coatings, to reduce adhesion of cells and protein. The coatings may incorporate drugs and/or other agents that are released at a sustainable rate ranging from a period of 1 week to 6 months. The coatings may comprise inhibitors of fibrosis, including, for example, TGF-β, other cytokines expressed as mediators of the inflammatory cascade, SMA, and/or integrins.

In some embodiments, the multilayer coating includes pendant hydroxyl groups, with the number density of hydroxyl groups varying between the layers of the coating. Preferably the number density is the lowest in the layer closest to the surface of the implant (i.e., the innermost layer of the coating) and highest at the uppermost layer of the coating.

The multilayer coating may be deposited on the sensing system through a vacuum deposition process (e.g., chemical vapor deposition or physical vapor deposition).

Gel or Liquid Filling Material

The filling material (e.g., filling material 114 and 214 in FIGS. 1A and 2A, respectively) in the sensing system is a viscous liquid or gel with a thickness of about 5 μm to about 500 μm (e.g., about 5 μm to about 25 μm). The filling material is an inert or substantially inert material. In one example, the filling material is a polymerized siloxane (also called a silicone, e.g., polydimethylsiloxane (PDMS)). In another example, the filling material is a hydrogel (e.g., a polyacrylate, a polymethacrylate, a polyurethane, a polyether, a polyester, a polyvinyl compound, a polycarbonate, or an epoxide).

The liquid or gel filling material may fill one or more voids in the sensing system between the multilayer coating and the other components. In one example, the filling material may be a soft silicone gel. The silicone gel may be inert so as to not cause any substantial changes to the sensor elements over a period of ten years or more. The silicone gel may pose less of a safety risk than a liquid because it is less likely to leak out of the sensing system while implanted. The thickness of the silicone gel may vary from about 1 μm to about 25 μm (e.g., 1 μm, 2 μm, 5 μm, 10 μm, 20 μm, or 25 μm). The elastic modulus of the silicone gel may vary from about 0.4 kPa to about 300 kPa. The pressure in the environment of the sensing system is transmitted through this range of gel thicknesses and elastic moduli.

The filling material may be used to keep the multilayer coating in mechanical contact with the pressure sensor's sensing elements so that the pressure sensor is able to measure pressure while encapsulated by the coating. The force exerted by the pressure is transmitted through the coating and the filling material to the sensing elements in the pressure sensor. The pressure sensor can accurately measure pressure through a significant range of gel or liquid thicknesses and levels of rigidity.

As shown in FIG. 1A, in addition to the perimeters formed by the coiled antenna, the pressure sensor may include its own perimeter walls to form a separate container in which the same or a different filling material (also called a sensor filling) is disposed on a surface of the sensor including the sensing elements. In this way, two or more different filling materials are used in different parts of the sensing system.

In another embodiment, shown in FIG. 2A, a single liquid or gel filling material may fill all of the voids in the sensing system encapsulated by the coating. In another embodiment, shown in FIG. 4A, a liquid or gel filling material fills the void between the pressure sensor and the coating and other voids between other electronic components and the coating may be filled with air or an inert gas.

The filling material may include a small amount of water in a weight percent of about 0.001% by weight to about 5% by weight (e.g., about 0.002%, 0.005%, 0.01%, 0.05%, 0.1%, 0.5%, 1%, or 5%). The addition of water into the filling material may prevent or substantially reduce pressure sensor drift by passivating the sensing elements in the pressure sensor and/or by reducing the chemical potential for diffusion of water from outside of the sensing system to inside of the sensing system. For example, the filling material infused with water may reduce drift to values of less than about 2 mm Hg per year.

Implantation

The sensing system may be a standalone implant or embedded into other implants (e.g., existing FDA-approved implants). The sensing system is configured to be implanted into a subject (e.g., a human or an animal) to measure cardiovascular parameters such as BP or pressure in a vascular structure or heart chamber. The measured pressure is presented as waveform data that captures the pressures generated throughout the cardiac cycle. The measured may be used to diagnose or manage specific cardiovascular diseases (e.g., chronic hypertension, congestive heart failure, primary pulmonary hypertension, and others. The sensing system may autonomously and continually monitor pressure within the cardiovascular system while implanted.

In one embodiment, the sensing system may be implanted into a subject so that it resides on the surface of a blood vessel in the subject to measure blood pressure in that blood vessel. The blood vessel may be a peripheral vessel or a central vessel. The advantages of placing the sensing system on a peripheral blood vessel include easy access for implantation and explantation. The advantages of placing the sensing system on a central blood vessel include the ability to monitor blood pressure in a central blood vessel.

In another embodiment, the sensing system may be implanted so that it resides inside of a chamber of the heart (e.g., an atrium, or ventricle). For example, the sensing system may be implanted into the left atrium for management of CHF. The sensing system may be mounted to a structure (e.g., a stent, a catheter, a prosthetic valve, or other intracardiac or intravascular device).

In another embodiment, the sensing system may be implanted so that it resides inside of a blood vessel (e.g., an artery or a vein). In this embodiment, the sensing system may directly measure intra-arterial pressure. For example, the sensing system may be implanted into a pulmonary artery and measure pulmonary artery pressure, for the management of CHF.

The sensing system may have a capsule shape, a flat cylindrical shape, like the device in FIG. 1A, a combination of the two, like in FIG. 2A, or another shape. The sensing system has dimensions of about 3 mm to about 20 mm in length, about 2 mm to about 5 mm in width, and about 2 mm to about 3 mm in height. The volume of the sensing system may have a volume of about 10 $mm^3$ to about 300 $mm^3$.

Figure 8A:
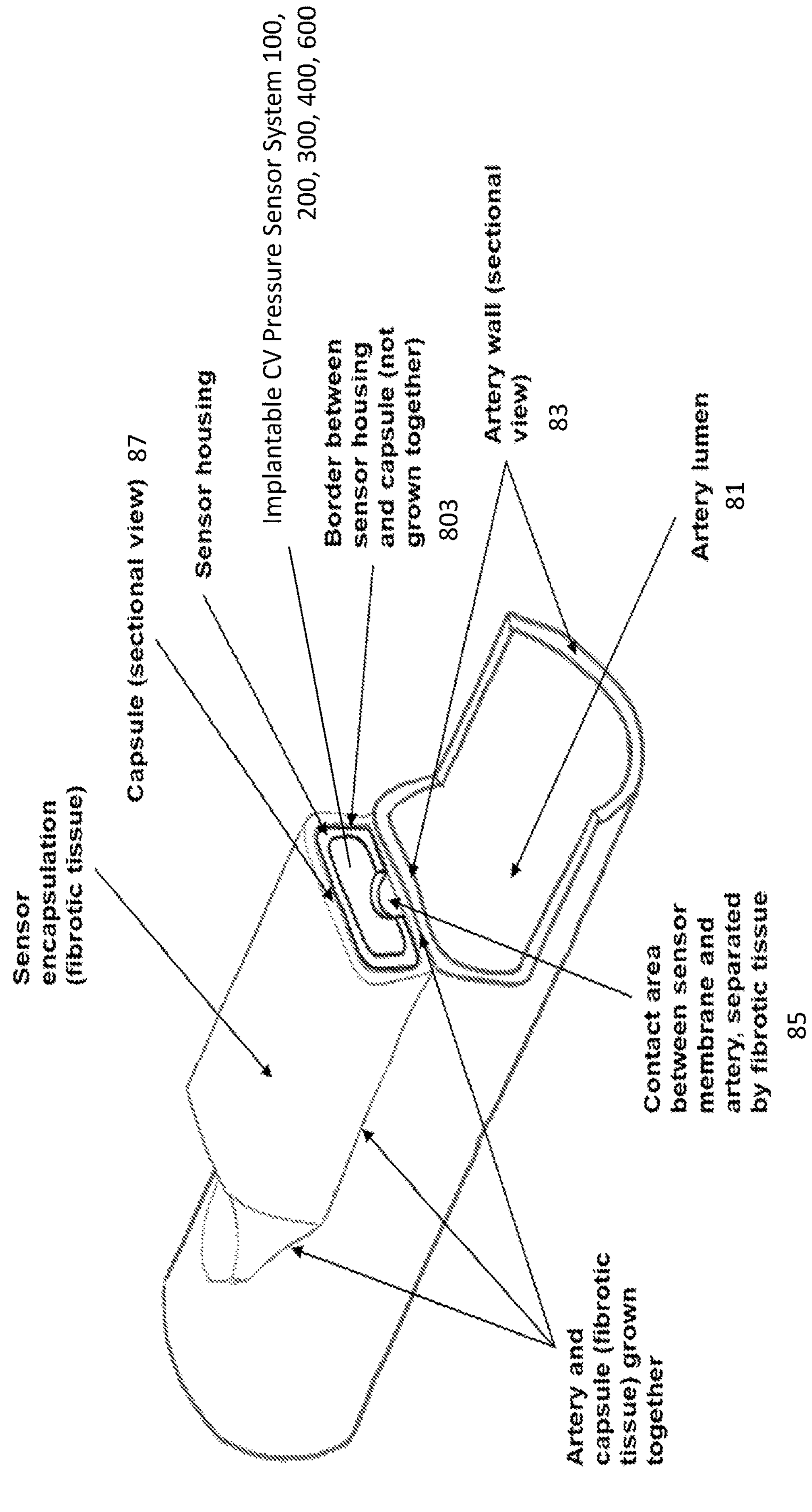
FIG. 8A illustrates an implantable cardiovascular pressure sensing system placed external to an artery for measuring blood pressure within the artery.
Figure 8B:
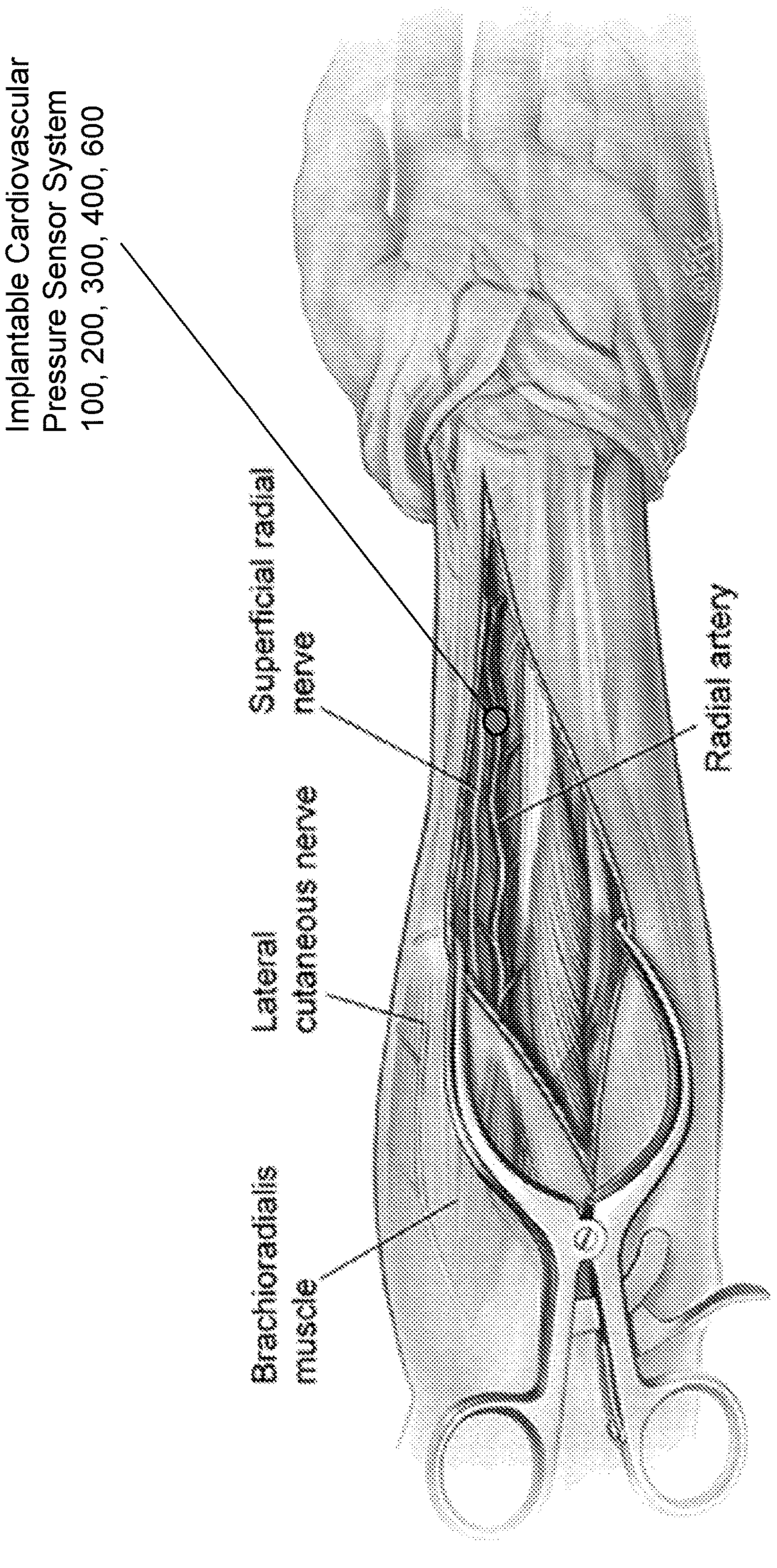
FIG. 8B illustrates implant sites for an implantable cardiovascular pressure sensing system in a human arm.
Figure 8C:
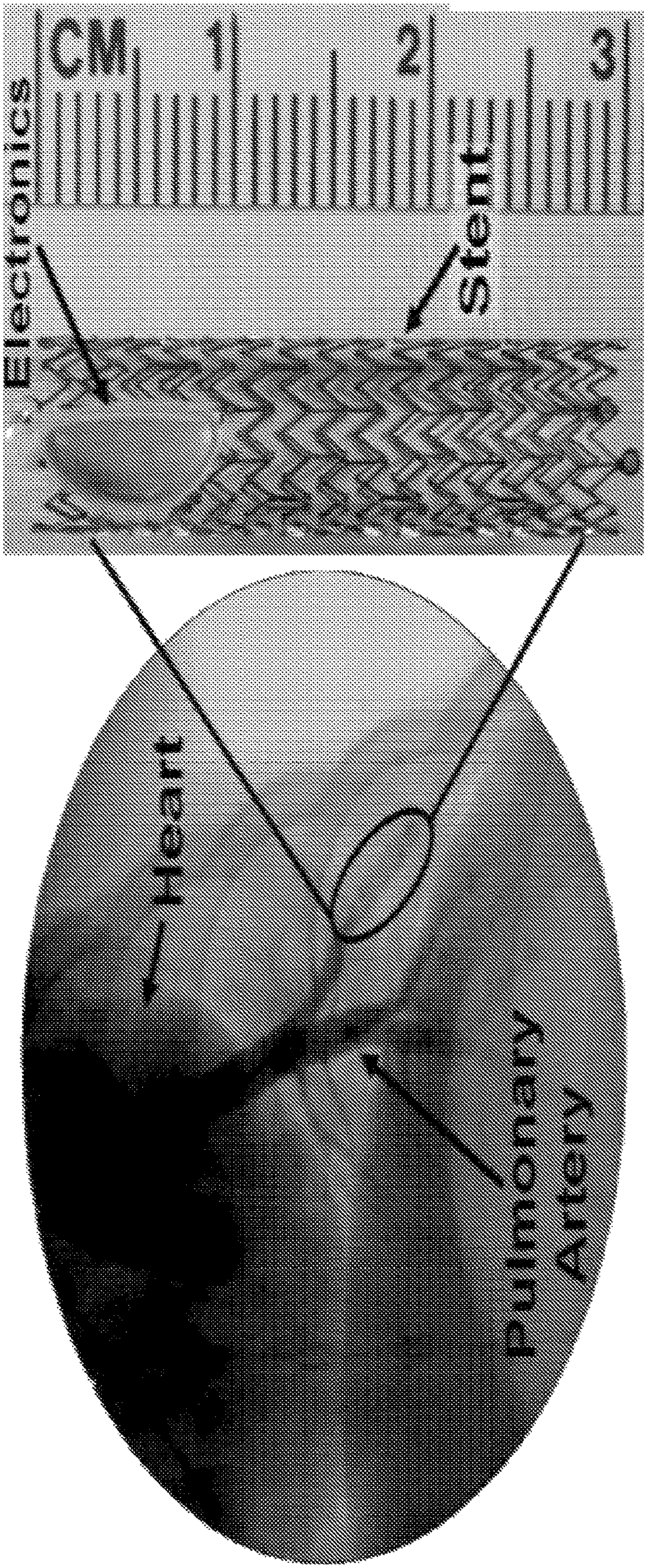
FIG. 8C illustrates an implant site for an implantable cardiovascular pressure sensing system in a pulmonary artery in the heart.

FIGS. 8A-8C show different example locations where an implantable cardiovascular pressure sensing system may be implanted. Generally, an inventive sensing system can measure pressure in any or many different arteries. This includes peripheral arteries (such as the radial, brachial, and others) and central, major, or great arteries such as the aorta, great vessels, iliac, femoral, carotid and others. An inventive implantable pressure sensing system can also be placed on or in an arterial substitute, such as a vascular graft or endograft.

FIG. 8A is a cutaway cross section of an implantable cardiovascular pressure sensing system (e.g., sensing system 100, 200, 300, 400, or 600) after implantation and fibrotic encapsulation along an exterior wall 83 of an artery. The artery wall 83 separates the sensing system from the artery lumen 81, with fibrotic tissue 85 separating the contact area between the sensing system's pressure-sensing surface and the artery. The sensing system may have a sensor housing (e.g., a multilayer coating 140, 240) that is encapsulated by a capsule 89 of fibrotic tissue, which is grown together with the artery itself.

FIG. 8B shows the sensing system may be placed on one or more arteries in the forearm. It can also be placed in other limbs or other parts of the body. FIG. 8B shows additional locations where the sensing system may be implanted onto the radial artery. The device can also be implanted on top of any artery in the body where measurement of pressure in the target artery is of clinical importance.

The implantable cardiovascular pressure sensing system can be placed on or in proximity to the vessel wall using straightforward percutaneous approaches. Similarly, the implantable cardiovascular pressure sensing system can be placed on any selected targeted vessel with a direct or open approach.

The implantable cardiovascular pressure sensing system can be fixed in place with the use of adjuncts, such as tissue adhesives like Bio Glue, or direct suture technique.

FIG. 8C shows the sensing system placed in a chamber of the heart and mechanically coupled to a stent. In one version, placing more than one sensing system in a patient may be desirable, for example, with one sensing system placed in an artery in a limb, another embedded into a first heart valve, and/or another implanted into a second heart valve or heart prosthesis. For example, one sensing system may be placed in the left atrium of the heart, and another may be placed in the left ventricle side of a mitral valve prosthesis.

Figure 8D:
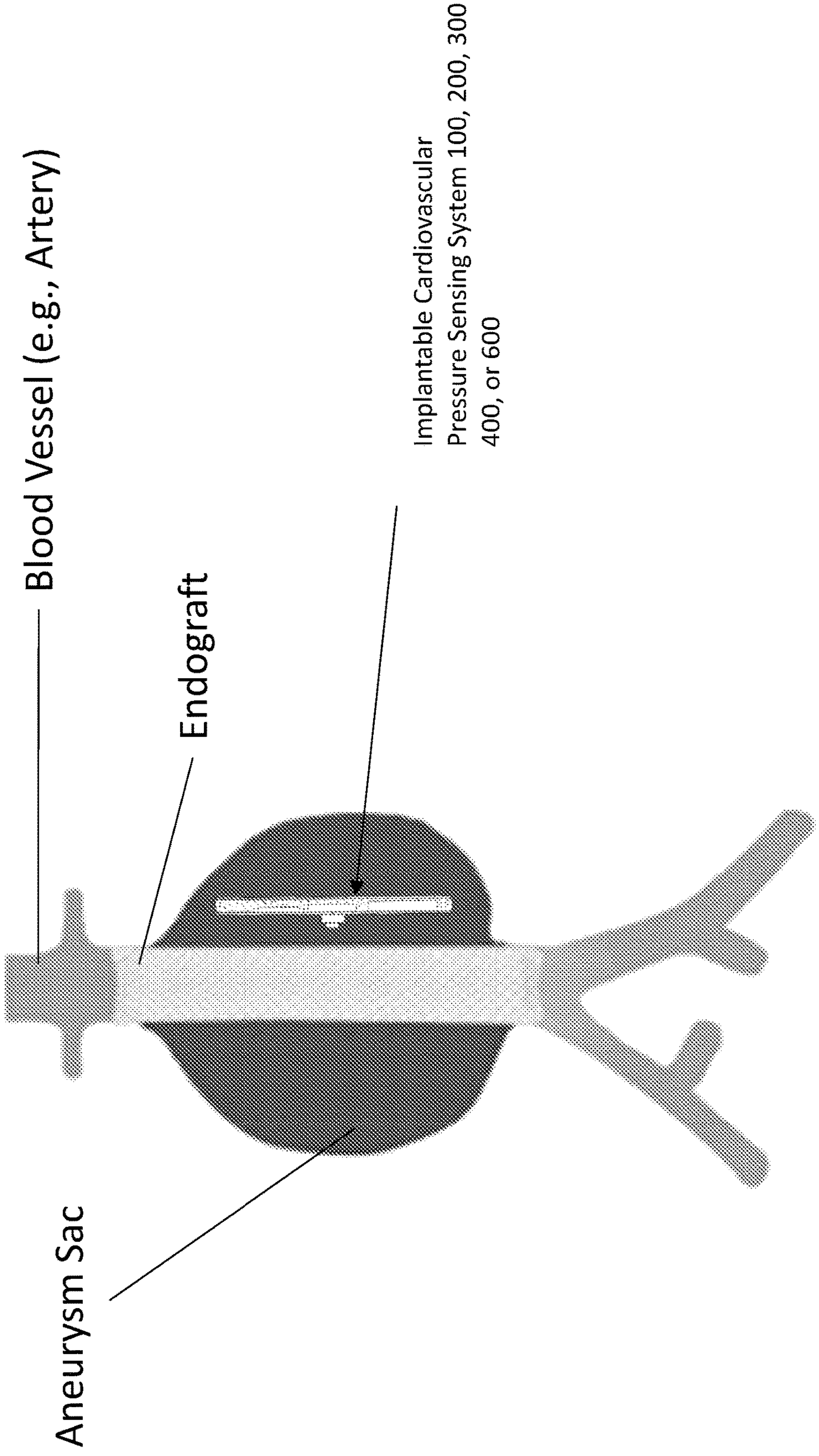
FIG. 8D shows an implantable cardiovascular pressure sensing system implanted in an aneurysm sac.
Figure 9A:
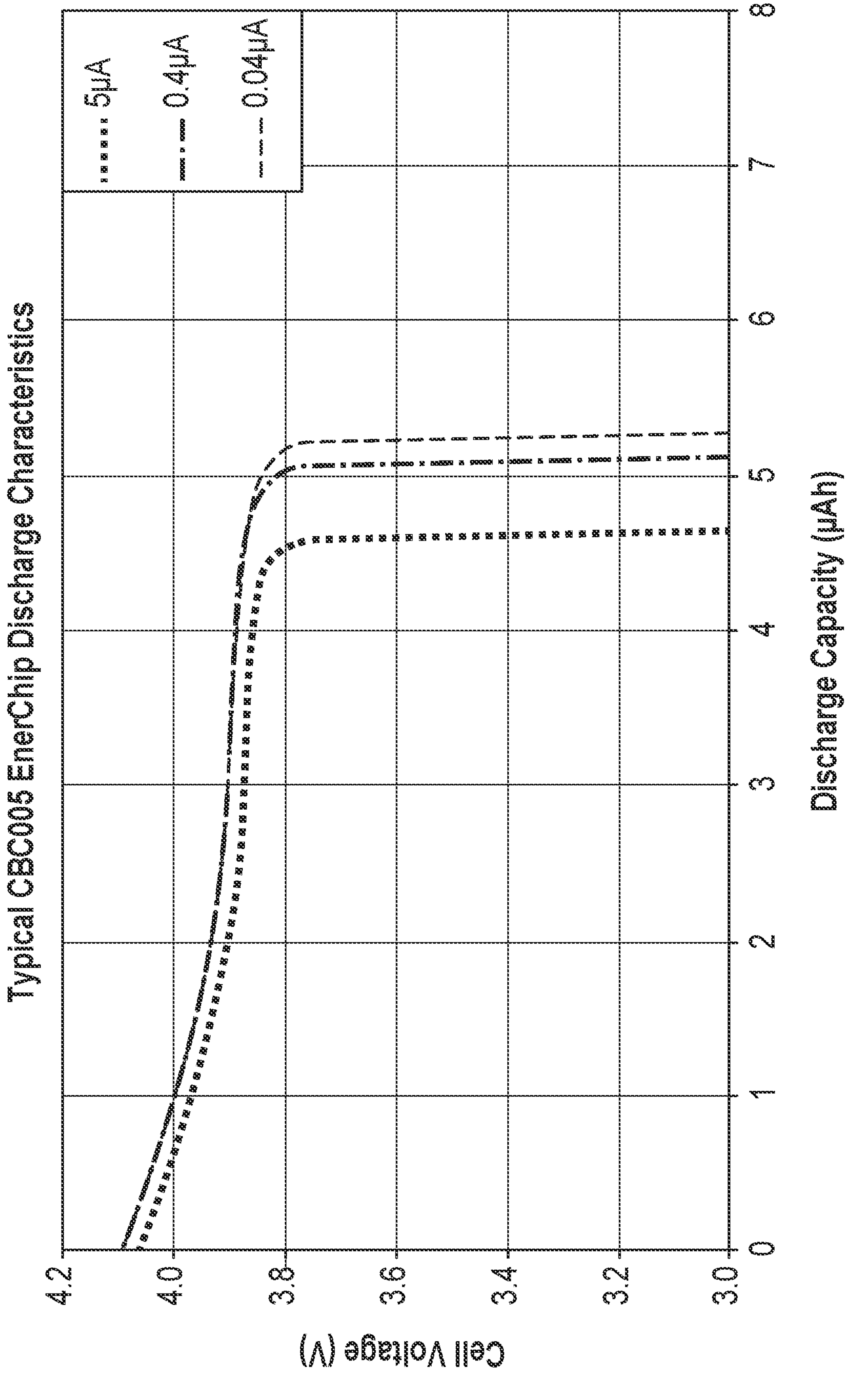
FIG. 9A is a graph of the discharge voltage profile of a rechargeable battery suitable for use as a power supply in an implantable cardiovascular pressure sensing system.
Figure 9B:
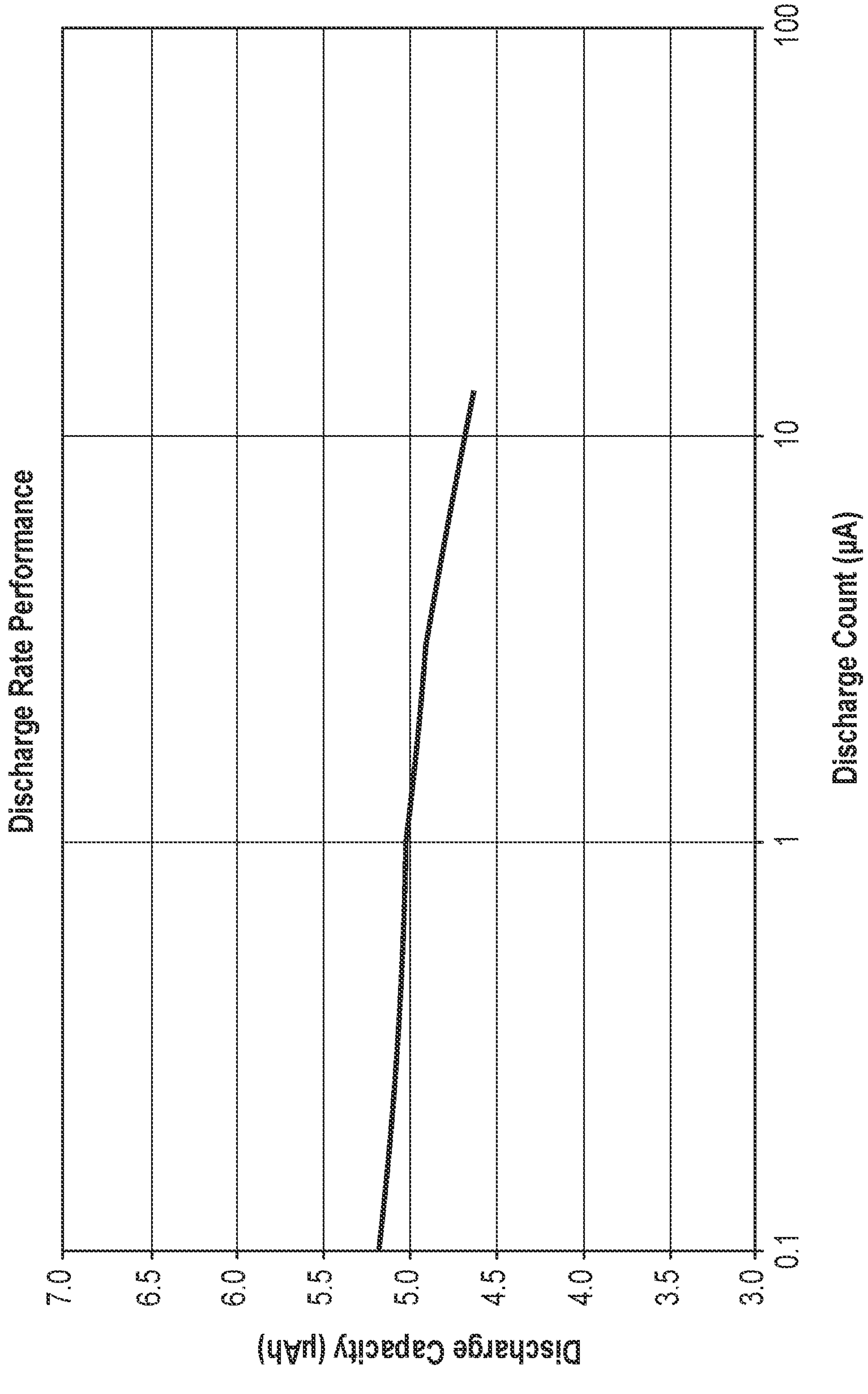
FIG. 9B is a graph of discharge rate performance of the rechargeable battery in FIG. 9A.

FIG. 8D shows a sensing system placed in an aneurysm sac. An aneurysm is an abnormal swelling or bulge in the wall of a blood vessel, such as the aorta or another artery. An aneurysm can be treated by implanting an endograft, which is a metallic stent covered in polytetrafluoroethylene or another suitable prosthetic graft material, that extends within the blood vessel past both ends of the aneurysm and guides blood through the blood vessel. The bulging portion of the blood vessel outside the endograft is the aneurysm sac and can hold an implanted sensing system oriented with its (primary) pressure sensor facing the endograft.

The pressure sensor in the sensing system may be calibrated on the day of implantation. Once the sensing system is implanted, the pressure sensor in the sensing system may be recalibrated by comparing the sensing system's measurements to those acquired using a conventional method of measuring blood pressure (e.g., auscultation with a sphygmomanometer). As an example, the sensing system may be calibrated on the date of implantation and then re-calibrated approximately 4 weeks to about 6 weeks after implantation. The implanted sensing system can be re-calibrated (e.g., by a physician) at intervals of about 6 months to about 2 years (e.g., 6 months, 1 year, 1.5 years, or 2 years) if there is a concern regarding sensor drift.

In another example, a spacer may be used to fix the distance between the implanted sensing system and the outer surface of the artery when the sensing system is implanted. The spacer may be configured to dissolve or degrade over a set period of time determined by the length of time it takes to secure the sensing system, either via fibrotic tissue buildup or glue, thereby fixing the distance of the sensing system from the surface of the artery.

Using a Sensing System

The rechargeable battery may have a discharge capacity of about 4 to about 500 μAh at currents of 0.04 μA to about 5'000 μA and a lifetime of about 15 years The battery may be safely recharged at a rate of about 0.2 C to about 10 C and may be recharged as many as about 2000 times or about 3000 times before failing.

Figure 10:
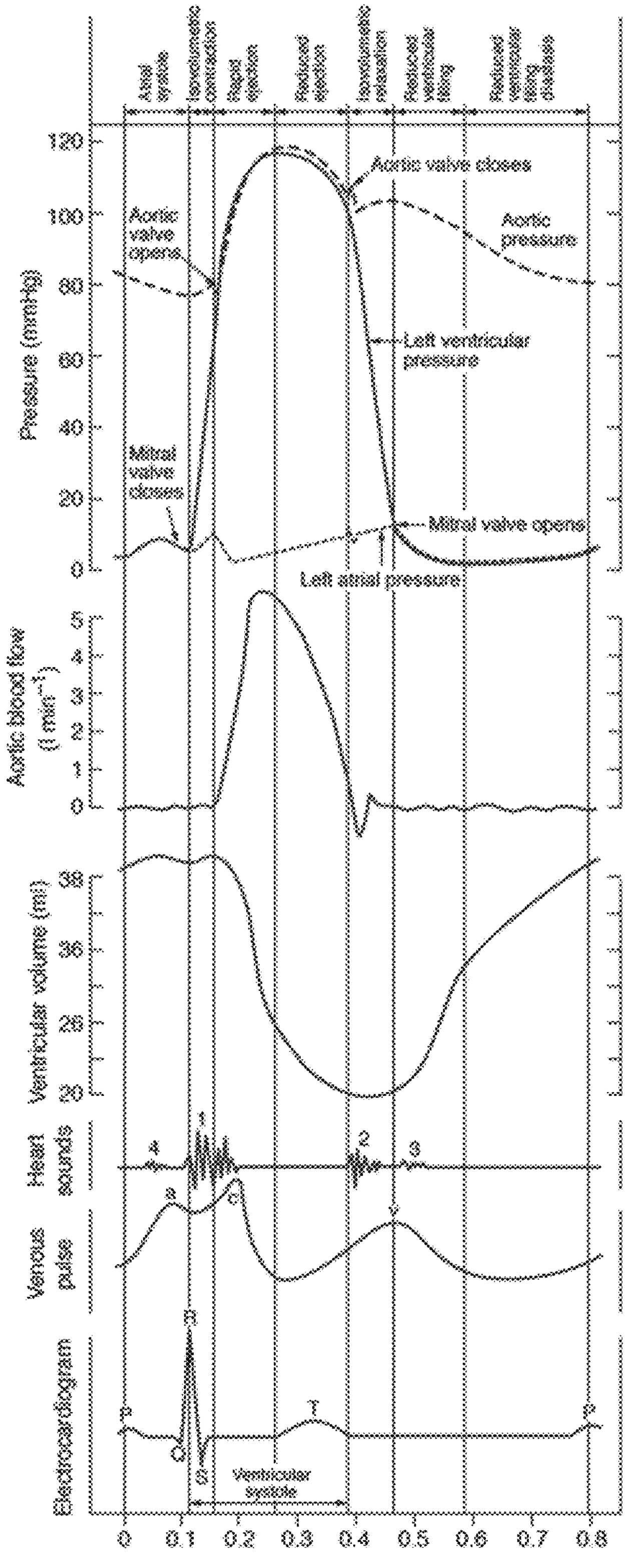
FIG. 10 is a graph of the pressure waveform over the cardiac cycle.

FIG. 10 is a graph of the pressure waveform over the cardiac cycle. By measuring the pressure inside of the cardiovascular system, the sensing system can determine heart rate, blood pressure, and heart function. The sensing system may measure pressure waveform data over the cardiac cycle. For example, the sensing system can measure 64 data points every second and generate 8 complete waveforms every minute.

Figure 11:
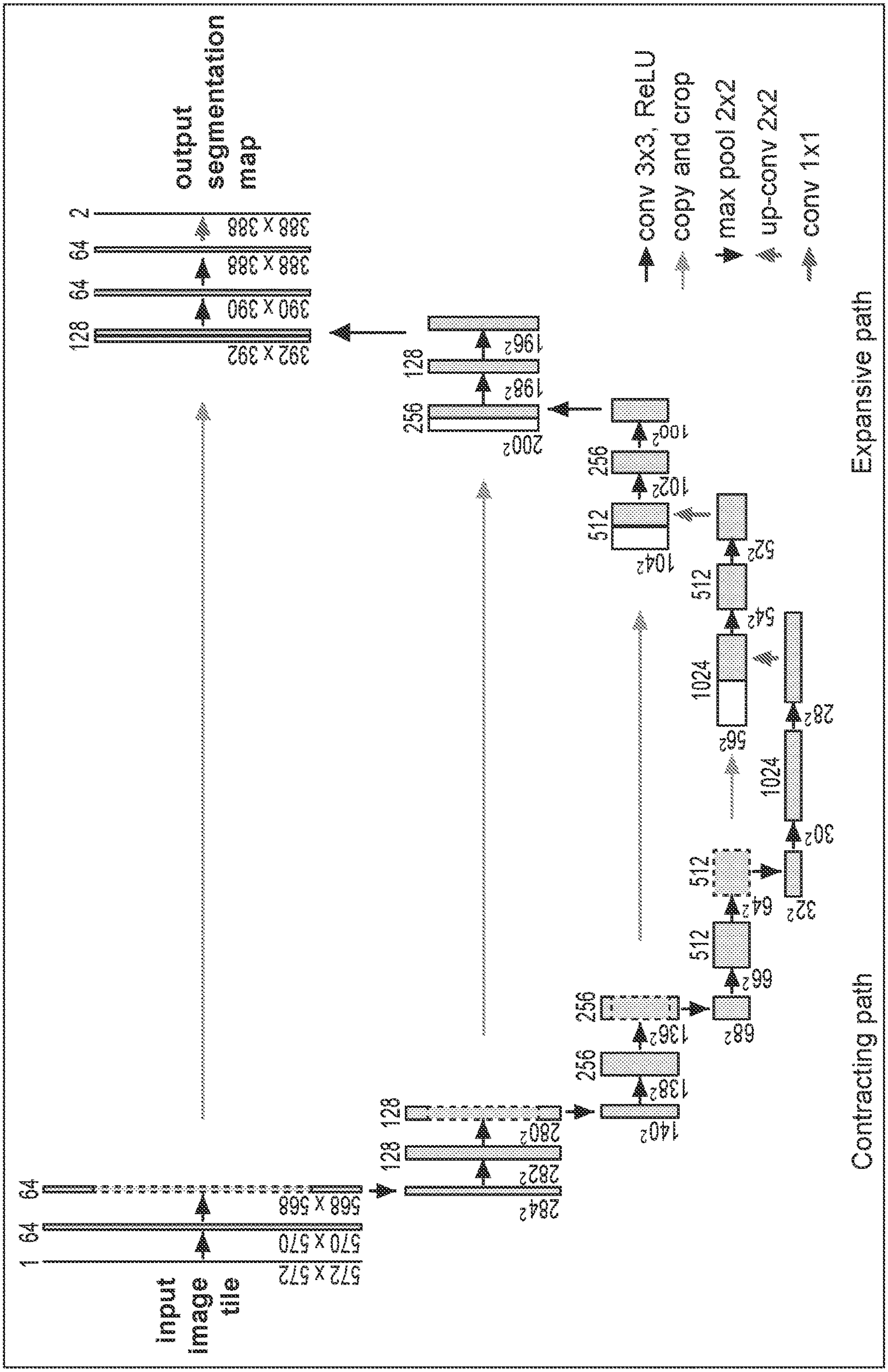
FIG. 11 illustrates a neural network architecture for processing signals from an implantable cardiovascular pressure sensing system.

FIG. 11 illustrates a neural network architecture (NNA) for processing data signals from the cardiovascular pressure sensing system with the external device. The NNA may use Wave-U-Net, an adaptation of the U-Net Artificial Intelligence (AI) architecture to the one-dimensional time domain, which repeatedly resamples raw data to compute and combine features at different time scales. This approach allows accurate measurement of critical contributors to the blood pressure waveform, occurring at different phases of the overall waveform. The neural network may be trained using waveforms ("Ground Truth") created from direct intra-arterial pressure measurement from the sensing system and sphygmomanometer data. Reference data may serve as ground truth and may be cross-checked and verified using the neural network. Test data may be obtained by smoothing and filtering data from sensing system. Ground truth data may be degenerated to closely approximate the test data. Degenerated ground truth data may be augmented with Ground Truth Annotation. Annotated test data may be used to train the neural network. Degenerated and augmented data and annotation may extend the training set. The neural network may then be tested using manually annotated data from the sensing system and the results may be compared to the Ground Truth. Once the neural network has been trained and tested, it can be deployed on a processor in an implantable cardiovascular pressure sensing system or in an external device that receives pressure measurements from an implantable cardiovascular pressure sensing system.

Figure 12:
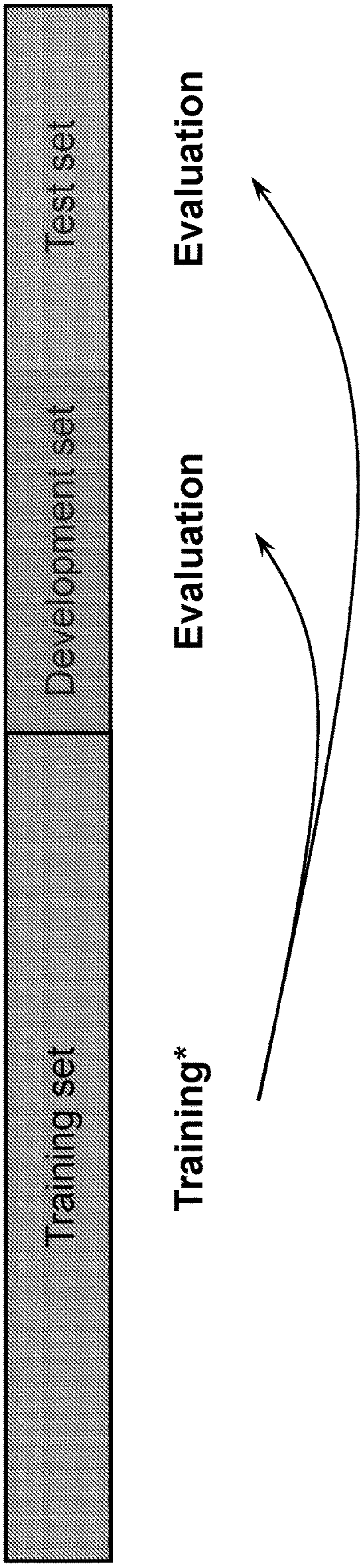
FIG. 12 illustrates a method of training the neural network in FIG. 11.

FIG. 12 illustrates a method of training the neural network in FIG. 11. The neural network may use manually annotated interferogram data. The data may be subdivided into subsets. One subset may be an initial training data set. Additional subsets may be development sets. Another subset is a test set to test the trained neural network. After initial training with the training data set, the development sets may be combined to create a larger training set, and the training may be repeated. The trained neural network may be tested using the test set.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/of" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An implantable cardiovascular pressure sensing system for implantation within a mammalian subject, the implantable cardiovascular pressure sensing system comprising:

a planar rigid carrier having a first side, a second side, a thickness between the first side and the second side of the planar rigid carrier, and an edge running perpendicular to both the first side and the second side of the planar rigid carrier along the thickness, wherein the planar rigid carrier comprises a printed circuit board;

a pressure sensor with a sensing surface, the pressure sensor mounted to the first side of the planar rigid carrier to measure a pressure of about 0 mm Hg to about 250 mm Hg over atmospheric pressure within a cardiovascular system of the mammalian subject;

an accelerometer mounted to the planar rigid carrier to measure an acceleration of the implantable cardiovascular pressure sensing system;

circuitry, operably coupled to the pressure sensor and the accelerometer and mounted to the planar rigid carrier, to identify motion artefacts in pressure data collected by the pressure sensor based on the acceleration measured by the accelerometer and to remove the motion artefacts from the pressure data;

a power supply, operably coupled to the circuitry and mounted to the planar rigid carrier, to provide electrical power to the circuitry;

a coil antenna, operably coupled to the circuitry and the power supply, to transmit the pressure data to a device external to the mammalian subject, the coil antenna being positioned on the first side of the planar rigid carrier along the edge of the planar rigid carrier and forming a wall extending perpendicular to the first side of the planar rigid carrier and surrounding the pressure sensor, the accelerometer, the circuitry, and the power supply; and a deformable multilayer coating surrounding and hermetically sealing the implantable cardiovascular pressure sensing system, the deformable multilayer coating comprising alternating layers of a polymer and a ceramic, wherein the implantable cardiovascular pressure sensing system is configured to be implanted on an external surface of a blood vessel such that the pressure sensor is maintained between the planar rigid carrier and the external surface of the blood vessel to measure pressure within the blood vessel, wherein the sensing surface of the pressure sensor extends beyond the wall formed by the coil antenna towards the external surface of the blood vessel, and wherein the deformable multilayer coating is configured to transmit pressure from the blood vessel to the pressure sensor.

2. The implantable cardiovascular pressure sensing system of claim 1, wherein the polymer comprises parylene-C and the ceramic comprises $SiO_x$.

3. The implantable cardiovascular pressure sensing system of claim 1, further comprising:

a gel and/or liquid disposed between the sensing surface of the pressure sensor and the deformable multilayer coating.

4. The implantable cardiovascular pressure sensing system of claim 3, further comprising:

filling material disposed at least partially on the circuitry and the power supply.

5. The implantable cardiovascular pressure sensing system of claim 3, wherein the gel has an elastic modulus of about 0.4 kPA to about 300 kPa.

6. The implantable cardiovascular pressure sensing system of claim 3, wherein the gel and/or liquid comprises a silicone gel.

7. The implantable cardiovascular pressure sensing system of claim 1, wherein the deformable multilayer coating is disposed conformably over the implantable cardiovascular pressure sensing system.

8. The implantable cardiovascular pressure sensing system of claim 1, wherein the coil antenna is configured to operate at a fixed frequency in a range of 100 kHz to 5.2 GHz.

9. The implantable cardiovascular pressure sensing system of claim 1, wherein the circuitry is further configured to remove the portion of the pressure data subjected to motion artifacts.

10. The implantable cardiovascular pressure sensing system of claim 1, wherein the blood vessel is at least one of an artery, a vein, or a synthetic blood vessel.

11. The implantable cardiovascular pressure sensing system of claim 1, wherein the implantable cardiovascular pressure sensing system occupies a volume of about 10 $mm^3$ to about 300 $mm^3$.

12. The implantable cardiovascular pressure sensing system of claim 1, wherein the implantable cardiovascular pressure sensing system has dimensions of about 3 mm to about 20 mm in length, about 2 mm to about 5 mm in width, and about 2 mm to about 3 mm in height.

13. The implantable cardiovascular pressure sensing system of claim 1, wherein the circuitry comprises an application-specific integrated circuit (ASIC).

14. The implantable cardiovascular pressure sensing system of claim 1, further comprising:

a temperature sensor, operably coupled to the circuitry and mounted to the planar rigid carrier, to measure an internal temperature of the mammalian subject.

15. The implantable cardiovascular pressure sensing system of claim 1, further comprising:

an oxygen sensor, operably coupled to the circuitry and mounted to the planar rigid carrier, to measure a blood oxygen level of the mammalian subject.

16. The implantable cardiovascular pressure sensing system of claim 1, wherein the pressure sensor is a first pressure sensor, and further comprising:

a second pressure sensor, operably coupled to the circuitry and mounted to a second side of the planar rigid carrier, to record pressure at a different location than the first pressure sensor.

17. The implantable cardiovascular pressure sensing system of claim 1, wherein the coil antenna is configured to supply power to the power supply from a wireless power source and to wirelessly transmit data to an external device.

18. The implantable cardiovascular pressure sensing system of claim 1, in combination with an atmospheric pressure sensor to measure variations in the atmospheric pressure.

19. The implantable cardiovascular pressure sensing system of claim 18, wherein the device external to the mammalian subject is configured to receive an indication of the variations in the atmospheric pressure and to compensate the pressure data for the variations in the atmospheric pressure based on the indication.

20. The implantable cardiovascular pressure sensing system of claim 1, wherein the pressure is a fluid pressure.

21. The implantable cardiovascular pressure sensing system of claim 1, wherein the implantable cardiovascular pressure sensing system is attached to the external surface of the blood vessel through at least one of fibrotic encapsulation, an adhesive, or a suture technique.

22. The implantable cardiovascular pressure sensing system of claim 1, wherein the implantable cardiovascular pressure sensing system is longitudinal in shape to fit on top of the external surface of the blood vessel.

23. The implantable cardiovascular pressure sensing system of claim 1, wherein the pressure is waveform pressure data.

24. The implantable cardiovascular pressure sensing system of claim 1, wherein the pressure sensor is a microelectromechanical system (MEMS) pressure sensor.

25. The implantable cardiovascular pressure sensing system of claim 24, wherein the MEMS pressure sensor is a capacitive pressure sensor.

26. The implantable cardiovascular pressure sensing system of claim 24, wherein the MEMS pressure sensor is a piezoelectric pressure sensor.

27. A method of measuring cardiovascular pressure with an implanted cardiovascular pressure sensing system, the method comprising:

collecting cardiovascular pressure data inside of a cardiovascular system of a mammalian subject with a pressure sensor with a sensing surface, the pressure sensor implanted external to a blood vessel of the cardiovascular system, the pressure sensor mounted to a first side of a planar rigid carrier that is proximal to an exterior wall of the blood vessel of the cardiovascular system such that the pressure sensor is maintained between the planar rigid carrier and the exterior wall of the blood vessel of the cardiovascular system, wherein the planar rigid carrier comprises a printed circuit board and the planar rigid carrier has a second side, a thickness between the first side and the second side of the planar rigid carrier, and an edge running perpendicular to both the first side and the second side of the planar rigid carrier along the thickness;

measuring motion of the mammalian subject with an accelerometer mounted to the planar rigid carrier;

identifying a motion artefact in the cardiovascular pressure data based on the motion of the mammalian subject;

compensating the motion artefact in the cardiovascular pressure data;

wirelessly transferring the cardiovascular pressure data from the implanted cardiovascular pressure sensing system to a device external to the mammalian subject via a coil antenna, the coil antenna being positioned on the first side of the planar rigid carrier along the edge of the planar rigid carrier and forming a wall extending perpendicular to the first side of the planar rigid carrier and surrounding the pressure sensor and the accelerometer;

collecting mass measurements on a surface of the implanted cardiovascular pressure sensing system with a mass sensor mounted to the planar rigid carrier; and compensating the cardiovascular pressure data using the mass measurements.

28. The method of claim 27, wherein collecting the cardiovascular pressure data comprises making 1 to 50 cardiovascular pressure measurements about every 10 minutes to about every 24 hours.

29. The method of claim 27, wherein collecting the cardiovascular pressure data comprises collecting the cardiovascular pressure data over a complete cardiac cycle.

30. The method of claim 27, further comprising:

wirelessly recharging a power source mounted to the planar rigid carrier of the implanted cardiovascular pressure sensing system.

31. The method of claim 27, further comprising:

processing the cardiovascular pressure data with an artificial neural network.

32. The method of claim 31, further comprising:

training the artificial neural network using the cardiovascular pressure data obtained from the implanted cardiovascular pressure sensing system.

33. The method of claim 27, further comprising:

programming a frequency and/or an interval at which the implanted cardiovascular pressure sensing system collects the cardiovascular pressure data.

34. The method of claim 27, further comprising:

collecting temperature measurements inside of the cardiovascular system of the mammalian subject with the implanted cardiovascular pressure sensing system.

35. The method of claim 27, wherein the pressure sensor is a first pressure sensor, and further comprising:

collecting internal pressure data with a second pressure sensor mounted to a second side of the planar rigid carrier; and compensating for pressure variations in the mammalian subject based on the internal pressure data from the second pressure sensor.

36. The method of claim 27, further comprising:

processing the cardiovascular pressure data using the device external to the mammalian subject.

37. The method of claim 36, wherein the processing the cardiovascular pressure data using the device external to the mammalian subject comprises at least one of calibrating the cardiovascular pressure data, compensating the cardiovascular pressure data, filtering the cardiovascular pressure data, or converting the cardiovascular pressure data.

38. The method of claim 27, wherein the compensating the motion artefact in the cardiovascular pressure data comprises correcting the cardiovascular pressure data to remove a motion artefact from the cardiovascular pressure data.

39. An implantable cardiovascular pressure sensing system for implantation within a mammalian subject, the implantable cardiovascular pressure sensing system comprising:

a rigid carrier;

a pressure sensor mounted to a first surface of the rigid carrier to measure a pressure of about 0 mm Hg to about 250 mm Hg over atmospheric pressure within a cardiovascular system of the mammalian subject;

a gel and/or liquid disposed on a sensing surface of the pressure sensor;

an accelerometer mounted to the rigid carrier to measure an acceleration of the implantable cardiovascular pressure sensing system;

circuitry, operably coupled to the pressure sensor and the accelerometer and mounted to the rigid carrier, to identify motion artefacts in pressure data collected by the pressure sensor based on the acceleration measured by the accelerometer and to remove the motion artefacts from the pressure data;

a power supply, operably to the circuitry and mounted to the rigid carrier, to provide electrical power to the circuitry;

an antenna, operably coupled to the circuitry and the power supply, to transmit the pressure data to a device external to the mammalian subject, wherein the antenna is a coil antenna surrounding the rigid carrier and forming a wall extending perpendicular to the first surface of the rigid carrier around a periphery of the first surface of the rigid carrier;

filling material disposed at least partially on the circuitry, the rigid carrier, and the power supply and contained within the wall formed by the antenna;

a multilayer coating forming an outer layer of and hermetically sealing the implantable cardiovascular pressure sensing system, the multilayer coating comprising alternating layers of a polymer and a ceramic, the multilayer coating disposed on top of the gel and/or liquid and the filling material; and a mass sensor, operably coupled to the circuitry and mounted to the rigid carrier, to measure a mass deposited on the pressure sensor.

40. The implantable cardiovascular pressure sensing system of claim 39, wherein the implantable cardiovascular pressure sensing system is configured to be implanted in or in the vicinity of the cardiovascular system and to measure pressure within the cardiovascular system.

41. The implantable cardiovascular pressure sensing system of claim 40, wherein the implantable cardiovascular pressure sensing system is configured to be implanted inside a blood vessel and to measure intra-arterial pressure.

42. The implantable cardiovascular pressure sensing system of claim 40, wherein the implantable cardiovascular pressure sensing system is configured to be implanted on an outer surface of a blood vessel such that the pressure sensor is maintained between the rigid carrier and the outer surface of the blood vessel to measure pressure within the blood vessel.

43. The implantable cardiovascular pressure sensing system of claim 40, wherein the implantable cardiovascular pressure sensing system is configured to be implanted inside of a chamber of a heart and to measure pressure within the chamber of the heart.

44. The implantable cardiovascular pressure sensing system of claim 40, wherein the implantable cardiovascular pressure sensing system is configured to be mounted to a structure.

45. The implantable cardiovascular pressure sensing system of claim 44, wherein the structure is at least one of a stent, a catheter, a prosthetic valve, an intracardiac device, an intravascular device, a vascular graft, or an endograft.

46. The implantable cardiovascular pressure sensing system of claim 40, wherein the implantable cardiovascular pressure sensing system is configured to be implanted in a space adjacent to a vascular structure.

47. The implantable cardiovascular pressure sensing system of claim 46, wherein the space adjacent to the vascular structure is an aneurysm sac.

48. The implantable cardiovascular pressure sensing system of claim 39, wherein the mass deposited on the pressure sensor is fibrous tissue.

49. The implantable cardiovascular pressure sensing system of claim 39, wherein the polymer comprises parylene-C and the ceramic comprises $SiO_x$.

50. The implantable cardiovascular pressure sensing system of claim 39, wherein the pressure sensor is a first pressure sensor, and further comprising:

a second pressure sensor, operably coupled to the circuitry and mounted to a second side of the rigid carrier, to record pressure within the mammalian subject at a different location than the first pressure sensor.

* * * * *